US011572494B2

(12) United States Patent
Corzani et al.

(10) Patent No.: US 11,572,494 B2
(45) Date of Patent: Feb. 7, 2023

(54) HOT-MELT ADHESIVES WITH IMPROVED ADHESION AND COHESION

(71) Applicant: Savare' I.C. S.r.l., Milan (IT)

(72) Inventors: Italo Corzani, Chieti (IT); Biagio Savare', Milan (IT)

(73) Assignee: Savare' I.C. S.r.l., Milan (IT)

( * ) Notice: Subject to any disclaimer, the term of this patent is extended or adjusted under 35 U.S.C. 154(b) by 250 days.

(21) Appl. No.: 16/775,354

(22) Filed: Jan. 29, 2020

(65) Prior Publication Data

US 2020/0165495 A1     May 28, 2020

Related U.S. Application Data

(63) Continuation-in-part of application No. 16/315,789, filed as application No. PCT/EP2017/066789 on Jul. 5, 2017, now Pat. No. 11,060,002.

(51) Int. Cl.

| | |
|---|---|
| *C09J 123/22* | (2006.01) |
| *A61L 15/24* | (2006.01) |
| *A61L 15/60* | (2006.01) |
| *B32B 7/12* | (2006.01) |
| *A61F 13/49* | (2006.01) |
| *A61F 13/539* | (2006.01) |
| *A61F 13/02* | (2006.01) |
| *A61F 13/47* | (2006.01) |
| *C08K 5/01* | (2006.01) |

(52) U.S. Cl.
CPC ......... *C09J 123/22* (2013.01); *A61F 13/0253* (2013.01); *A61F 13/47* (2013.01); *A61F 13/49* (2013.01); *A61F 13/539* (2013.01); *A61L 15/24* (2013.01); *A61L 15/60* (2013.01); *B32B 7/12* (2013.01); *A61F 2013/5395* (2013.01); *C08K 5/01* (2013.01)

(58) Field of Classification Search
CPC .... C09J 123/22; C09J 123/20; A61F 13/0253; A61F 13/47; A61F 13/49; A61F 13/539; A61F 2013/5395; A61L 15/24; A61L 15/60; A61L 15/42; A61L 15/585; B32B 7/12; B32B 2555/02; B32B 3/266; B32B 5/02; C08K 5/01; C08L 2205/025
See application file for complete search history.

(56) References Cited

FOREIGN PATENT DOCUMENTS

EP             314495 A   *   5/1989 ............ C09J 123/20

\* cited by examiner

*Primary Examiner* — Daniel H Lee
(74) *Attorney, Agent, or Firm* — Bay State IP, LLC

(57) ABSTRACT

Adhesive hot-melt formulations with a main polymeric component, of at least one isotactic metallocene butene-1 polymer composition, that has a low viscosity, and that has a bimodal composition, directly obtained during polymerization, in two consecutive and separate reaction steps.

Moreover, said hot-melts include less than 5% by weight of at least one viscosity modifier that is not solid at room temperature. Such unusually low level of said additives, surprisingly allows to attain substantially improved levels both of high adhesiveness and cohesion.

The adhesive hot-melt formulations include less than 5% by weight of a polyethylene wax or of a blend of polyethylene waxes, that characterized by a highly linear/non-branched structure and by an exceptionally low Polydispersity Index. The presence of such peculiar polyethylene waxes, that are partially incompatible with the butene-1 polymer composition, allows to use the disclosed hot-melt formulations even in the presence of fibrous or perforated substrates.

54 Claims, No Drawings

HOT-MELT ADHESIVES WITH IMPROVED ADHESION AND COHESION

CROSS REFERENCE TO RELATED APPLICATION

This application is a continuation-in-part application which takes priority from and claims the benefit of U.S. patent application Ser. No. 16/315,789 filed on Jan. 7, 2019 and which in turn is a U.S. National Phase under § 371 for International Application No. PCT/EP2017/066789 having an international filing date of Jul. 5, 2017, and from which priority is claimed under all applicable sections of Title 35 of the United States Code including, but not limited to, Sections 120, 363, and 365(c), and which in turn claims priority under 35 USC 119 to European Patent Application No. 16178432.7 filed on Jul. 7, 2016, European Patent Application No. 16178433.5 filed on Jul. 7, 2016 and Italian Patent Application No. 102017000030594 filed on Mar. 20, 2017.

BACKGROUND OF THE INVENTION

Field of the Invention

The present invention discloses new adhesive hot-melt formulations that comprise, as their main polymeric component, at least one isotactic metallocene butene-1 polymer composition, that has a low viscosity (and therefore a relatively low average molecular weight), and that has a substantially bimodal composition, directly obtained during polymerization, in two consecutive and separate reaction steps, where the first polymer (polymer A) of said compositionally bimodal polymer composition is an isotactic butene-1 homopolymer or an isotactic butene-1 copolymer with another olefin, while the second polymer (polymer B) is an isotactic copolymer of butene-1, with another olefin, with a chemical composition obviously different from A), qualitatively and/or quantitatively; said hot-melts further comprising less than 5% by weight of at least one viscosity modifier that is not solid at room temperature.

Description of the Related Art

In comparison with adhesive hot-melt formulations based on similar metallocenic butene-1 compositions, already disclosed in a part of the Prior Art (see below), the present adhesive hot-melt formulations, while still showing a low viscosity in the melt and excellent processability, exhibit also a new and unexpectedly enhanced combination between very high adhesiveness and cohesiveness that allows to use them even in particularly critical and demanding applications, in which the formulations, based on similar polymers, already disclosed by a part of the Prior Art, completely fail. Said particularly critical features, as unusually high adhesion and cohesion that are required in the adhesives, can be found e.g. in certain bonded parts/structures of hygienic absorbent articles (like baby and incontinent adult diapers), especially when it is needed to strongly bond between them (i.e. forming what is technically defined as a "laminate structure" or "laminate") two substrates that are porous or fibrous or two perforated plastic films, with holes having either a bidimensional or a tridimensional morphology; or to bond one of said porous or fibrous substrates or perforated films with an unperforated plastic film.

In order to ensure that the hygienic absorbent article has the global high softness required by the final user, said substrates (both with and without holes) must always be easily pliable and therefore very thin, as indicated by their very low basis-weight, generally lower than 50 $g/m^2$, often lower than 25 $g/m^2$ and not rarely even lower than 15 $g/m^2$. Moreover, in order to keep a very high "softness and pliability" even in the laminate structures, that are formed by adhering between them said substrates, it is necessary to apply, between the two substrates, also very small quantities of the adhesive, for example non greater than 15 $g/m^2$, preferably not greater than 10 $g/m^2$ and often even not greater than or below 5 $g/m^2$.

In such a way, it is possible that a contradiction arises between the characteristics of the used materials and the performances that are required in use; i.e. between the fact that certain bonded structures (laminates), that are formed by using low or very low quantities of an adhesive for bonding two very thin and pliable substrates, e.g. a plastic film bonded to a nonwoven, are required to withstand in use very high mechanical stresses, furthermore applied on very small areas. This situation typically occurs for example in the laminates, made by bonding a polyethylene film and a nonwoven, that form the external impermeable backsheet of a baby-diaper or of an incontinent adult diaper.

It is well clear to every person with at least an average skill in the manufacturing of hygienic absorbent articles and in the use of hot-melt adhesives in such manufacturing, that the above mentioned laminates, for example, are subjected in use to unusually high and critical mechanical stresses, that the bonded laminate structure must withstand without debonding and opening. And it is also clear that, just owed to the high softness and pliability of these laminate structures, the stresses that they must withstand in use are not only quantitatively very strong, but they are also applied on the laminate's adhesive bond according to an angle that may continuously change during time (e.g. in following the movements of the user), an angle that theoretically may vary between zero and 180 degrees, varying both in time and from point to point of the laminate structure.

Talking in terms of "adhesive properties", expressed according to the properties normally used in the science and technology of adhesives, this means that said laminate structures are subjected in use to debonding stresses that not only are quantitatively very strong, but that also require at the same time very high "Peel Strengths" and very high "Shear Strengths", two parameters that respectively express the high "adhesiveness" and the high "cohesiveness" of the adhesive that, inside these laminates, bonds the two forming substrates.

Besides the laminates used as outside impermeable backsheets in absorbent diapers, other laminate structures that, inside hygienic absorbent articles, are subjected in use to particularly strong and critical stresses for the adhesive, both in terms of adhesiveness (Peel Strength) and of cohesion (Shear Strength), are for example the laminates of the so called "Landing Zone", around the waist of the user, where the adhesive or "Velcro type" tapes that close the diaper are fixed.

The adhesive formulations according to the present invention show novel and surprising characteristics of simultaneous very high adhesiveness and cohesion, which properties allow to use them for manufacturing bonded laminate structures able to withstand very strong and particularly critical stresses, that are present e.g. in the above reported very demanding uses, in which other hot-melt adhesive formulations, even formulated with the same base polymers, but according to different criteria taught by the prior art, completely fail.

The novel adhesive formulations according to the present invention comprise unusually low quantities, compared to what taught and known in the prior art and practice, of viscosity modifiers that are not solid at 23° C., said low quantities being lower than 5% by weight. Even with such extremely small quantities of substances aimed at lowering the viscosity in the molten state, the present formulations show surprisingly low melt viscosities, that are fully comparable to the ones of analogous formulations having a much higher content of plasticizers and that are described in a part of the prior art; moreover they keep also an optimum processability in all the technologies used in the processing of hot-melt adhesives.

The drastic reduction in the level of not solid viscosity modifiers, compared to the prior art, not only improves in a fully unexpected way their adhesive and cohesive properties and makes them suitable to satisfy particularly critical uses, but also produces further and novel secondary beneficial effects. For example, positive effects of this type are the substantial disappearance of every possible demixing and bleeding during time of said viscosity modifiers from the core of the adhesive; and the substantial decrease or even the complete elimination of possible bad odors, that derive from the most volatile fractions of said viscosity modifiers having low molecular weights.

As a last observation, it is worthy to notice that the adhesive hot-melt formulations according to the present invention, even if they comprise very different quantities of some fundamentals components (like the not solid viscosity modifiers) from what taught by some prior art, keep and even increase the peculiar characteristic that is typical of the isotactic metallocene butene-1 polymer compositions used herein, i.e. the ability to further and strongly improve during time their initial adhesive, cohesive (mechanical) and rheological properties, due to a crystallization at room temperature, that is very slow and delayed in time and that typically completes in a few days.

In a further embodiment of the present invention, the herein disclosed hot-melt adhesive formulations, having a very low content of not solid viscosity modifiers, comprise also very small quantities, again non greater than 5% by weight, of a special type of polyethylene waxes having very peculiar chemical characteristics and molecular structures. Differently from analogous waxes, that have different compositions and different molecular structures, these peculiar waxes are able to regulate and control, in an exceptionally good and precise way, the contact and the partial penetration of the molten adhesive into a porous, fibrous or perforated substrate, in such a way avoiding the extremely negative phenomenon known, in the technology of adhesives, with the term "bleed-through" (see later for further details).

Definitions

The expressions "comprising" or "that comprise(s)" are used herein as open-ended terms, that specify the presence of what in the text follows said terms, but that does not preclude the presence of other ingredients or features, e.g. elements, steps, components, either known in the art or disclosed herein.

The expression "copolymer(s)" is used herein to mean a polymer in whose chemical composition are present at least two monomers or more than two monomers. Therefore, the term "copolymer(s)" means herein, unless the contrary is specifically stated, not only polymers in whose chemical composition are present two different monomers, but also polymers in whose chemical composition are present three, four, five or more different monomers.

The expressions "that is (are) not solid" are used herein to mean that a specific compound or material or ingredient or their blends, are in a physical state in which, even if they have a well definite volume, they do not have a fixed own shape, and they take the shape of the containers that contain them. Even in the case that they are sufficiently viscous to be temporarily shaped by themselves in any tridimensional shape, after being left at rest and without any external stress, apart from their own weight, they spontaneously flow and permanently deform, so to lose rather quickly (typically in a period of time that may vary between a few seconds and about one day) their initial shape, taking the shape of the containers that contain them (if these ones were not already full to the brim) or of the solid surface on which they are lying. Therefore this definition comprises all the materials that not only may be defined as "liquid" (both at high and low viscosity) according to the common meaning of this adjective, but also all those materials that, in the common language, are for example defined as "creamy", "pasty", "jelly-like", "fluid", "greasy", "semi-solid" and the like. A further way of defining in rheological terms what, in the present invention, is meant when a certain compound or material or ingredient or their blends are said to be "not solid" at room temperature, i.e. conventionally at the temperature of 23° C., is also by specifying that said "not solid" matters can be defined as "rheologically liquid", i.e. as defined in Rheology, that they, at the specified temperature of 23° C., have a Viscous Modulus G" that is greater than their Elastic Modulus G', or also, what is equivalent by definition, that their Tan Delta is greater than 1.

The equivalent expressions "Rheological Setting Point" or "Temperature of Rheological Setting" or "Temperature of the Crossing of the Moduli" or also "Crossover Point" and its symbol Tx, mean, in a rheological diagram in which are measured, as a function of temperature, the Elastic Modulus G', the Viscous Modulus G" and their ratio Tan Delta, the temperature at which the two Moduli cross (and in which therefore the value of Tan Delta is equal to 1) in the field of temperatures above room temperature. Said rheological diagram, when measured in decreasing temperature, with a sufficiently slow cooling rate (e.g. 2° C./minute, as done herein), mimics very well the phenomena that occur between the adhesive and a substrate in the real process of the application of a hot-melt adhesive from the molten state and of the subsequent creation of the adhesive bond, during the slow spontaneous cooling and setting/solidification. The "Rheological Setting Point" Tx identifies in particular the temperature at which the hot-melt adhesive, when applied in the molten state on a substrate, starts forming the final adhesive bond in the solid state.

The expression "Crossover Modulus" and its symbol Gc mean, again in the above mentioned rheological diagram, the absolute value (that by definition is identical), expressed in Pa or in MPa, that the Elastic Modulus and the Viscous Modulus have at the "Rheological Setting Point" Tx.

"Room temperature", if not specifically defined in a different way, means a temperature equal to 23° C.; and "room conditions" means the conditions of an environment at a controlled temperature and relative humidity, at 23° C. and 50% relative humidity.

"Absorbent hygienic articles" refer to devices and/or methods concerning disposable absorbing and non-absorbing articles, that comprise diapers and undergarments for incontinent adults, baby diapers and bibs, training pants, infant and toddler care wipes, feminine catamenial pads, interlabial pads, panty liners, pessaries, sanitary napkins, tampons and tampon applicators, wound dressing products, absorbent care mats, detergent wipes, and the like.

"Perforated films" refers to films, typically made of plastic materials, like polyethylene, that are perforated with multiple holes, and that can have both a bidimensional and a tridimensional structure, and with a typical hole size in the range between a few hundreds microns to about one millimeter, that are often used as components in absorbent hygienic articles.

"Fibrous substrates" refers to products having an essentially planar structure, formed by natural or synthetic fibers or their blends, both in the form of woven and of nonwoven fabrics, equally used as components in absorbent hygienic articles.

"Polydispersity Index" or "Molecular Weights Distribution Index" or "PDI" refers to a measure of the distribution of the molecular weight in a certain polymer. It is defined as the ratio between the weight average molecular weight Mw, and the number average molecular weight Mn: PDI=Mw/Mn. Greater values of PDI correspond to broader distribution curves of molecular weights and vice versa. Mw, Mn and therefore their ratio Mw/Mn=PDI, are measurable e.g. by Gel Permeation Chromatography (GPC).

"Open Time" of an adhesive refers, especially for a hot-melt adhesive, to the interval of time during which, after its application from the melt on a first substrate, the adhesive is able to form sufficiently strong adhesive bonds for the intended use, with a second substrate that is brought into contact under moderate pressure with the first one. It is evident that too short open times may make difficult-to-manage the application of an adhesive and the formation of sufficiently strong bonds. The open time of a holt-melt adhesive may be measured according to the test method ASTM D 4497-94, with the following conditions for the hot-melt adhesives disclosed herein:

Coating temperature of the adhesive film: 170° C.
Thickness of the adhesive film: 1 mm.

"Ring & Ball Softening Point" refers to the softening temperature of a material, measured according to the Method ASTM D 36-95.

Just for waxes, the "Softening Point" (called also "Dropping Point") is measured according to the Method ASTM D 3954-94.

The "Needle Penetration" of an adhesive is a measure of its softness. It is generally expressed as tenths of millimeter, dmm, and it is herein measured at 55° C., according to the Method ASTM D1321-04.

The dynamic viscosity of a molten or liquid material at a certain temperature is expressed as mPa·s and it is measured according to the Method ASTM D 3236-88.

The overall Adhesive Strength or "Peel Strength" is defined as the average strength per unit of width needed to separate two substrates, bonded by the adhesive under test, measured through a separation test made at a controlled and constant speed, and under a controlled and constant debonding angle. It is herein measured according to the Method ASTM D 1876-01, separating the two substrates under a debonding angle of 180 degrees, by applying a separation speed of the two substrates equal to 150 mm/minute, that means that the testing dynamometer is actually moving at a speed of 300 mm/minute. The two substrates used herein are a microporous polyethylene film, with a basis weight of 22 g/m², on which the molten adhesive is directly applied, by spraying or by slot-die extrusion, and on which a spun-bonded polypropylene nonwoven with a basis weight of 12 g/m² is immediately bonded. The measurement of the Peel Strength is made by recording the average strength needed to separate the two bonded substrates on a width of 50 mm.

The "Tensile Propertiers" or "Mechanical Properties in Tension" of all the materials disclosed herein, e.g. the hot-melt formulations, like the so called "Stress-Strain Curve", and the respective "Peak Stress" or "Ultimate Tensile Strength"; the "Stress at Break"; and "Elongation at Break" etc., are herein measured at 23° C. and 50% Relative Humidity, according to the following method. For each adhesive under test, five rectangular samples are prepared, by casting the molten adhesive at 170° C. into a silicone mold. Each rectangular sample has a length of 25 mm, a width of 6 mm and a thickness of 2 mm. After their solidification, the samples are taken out of the mold and are aged for five days at 23° C. and 50% Relative Humidity. For assessing its Stress-Strain curve to break, each sample is fixed with clamps, at its narrowest ends, to the shafts of a Rheometer Ares G2, available from TA Instruments, equipped for Tensile tests with the so called "Torsion Rectangular" geometry. The free length of the sample is 10 mm. The mobile upper shaft, that has a maximum further run of 60 mm (hence corresponding to a maximum readable strain of 600%), is started at an extension rate equal to 6 mm/minute.

These test conditions hence correspond to a Strain Rate of the sample equal to 0.01 s$^{-1}$, i.e. a frequency of 0.01 Hz, that, as well known to every person averagely skilled in the Rheology of adhesives, is the typical frequency at which said phenomena of slow detachment under load occur.

The tensile test is stopped either when the sample is fractured or when the rheometer has reached the maximum readable strain equal to 600%. For each Stress-Strain to break curve, the rheometer measures the maximum "Peak Stress" or "Ultimate Tensile Strength", the maximum Strain and it also calculates the area under the curve itself, area that is equal to the Toughness of the material, expressed in J/m³.

Finally, because (as shown later in more details) the peculiar isotactic metallocene butene-1 polymer composition, with a substantially bimodal composition, directly obtained during polymerization, in two consecutive and separate reaction steps, that are comprised in the hot-melt adhesive formulations of the present invention, as well as such hot-melt adhesive formulations themselves, substantially vary during time their adhesive, mechanical and rheological properties, owing to a slow crystallization at room temperature of said isotactic metallocene butene-1 polymer compositions, crystallization that completes between about one and about seven days and typically in about five days, it is necessary to distinguish between adhesive, mechanical and rheological "Properties at Time Zero" or "Initial Properties" (i.e. before the starting of said crystallization of the butene-1 polymer compositions) and the same properties measured e.g. after five days of aging at room conditions, i.e. after the completion of said crystallization.

In particular all the properties that are below defined as aged "at five days" for all the materials and laminate bonded structures disclosed herein, are meant as measured at 23° C. and 50% Relative Humidity on samples that have been aged for five days in a climatized room kept at 23° C. and 50% Relative Humidity. The five days are calculated from the moment when the adhesive sets from the molten state and therefore from the moment of production of the tested laminate bonded structures.

On the contrary, all the properties of materials and of laminate bonded structures that are below defined as "at Time Zero" or also as "Initial", are meant as measured, still at 23° C. and 50% Relative Humidity, but at a time that is not longer than three hours (180 minutes) after the moment when the adhesive sets from the molten state and therefore after the moment of production of the tested laminate bonded structures. In fact, it has been experimentally checked that the above mentioned slow spontaneous crystallization at room temperature of the peculiar metallocene butene-1 polymer compositions used herein, substantially does not start/does not occur in a significant way (and therefore does not produce any variation of properties detectable with any measurement method) within a few hours (indicatively up to three or four hours) from the moment of the solidification from the molten state of the polymer compositions and of the hot-melt adhesives that comprise them.

Other less usual parameters, that are measured according to specific methods, will be defined later, together with the detailed description of the methods for measuring them.

PRIOR ART

The isotactic homopolymers and copolymers (from butene-1 plus other olefins, e.g. ethylene) of polybutene-1 have been initially produced at an industrial scale and marketed by companies like Huls, Mobil, Witco and especially Shell, that since 1977 has been for long the main world manufacturer and whose production has now passed to LyondellBasell.

All the "old generation" productions of polybutenes-1 have been made by using Ziegler-Natta type catalysts, that create polymers at high or very high molecular weight and so at high or very high melt viscosities.

Recently a few manufacturers of polymers have abandoned the classic Ziegler-Natta catalytic systems and are using novel catalysts of the metallocene type, that allow to synthesize new-generation polybutenes-1 having novel and highly improved characteristics, like significantly lower and much more controlled average molecular weights (and therefore much lower melt viscosities); much smaller Polydispersity Indexes (and so much narrower distributions of the molecular weights) etc., all these properties producing also other improved characteristics of these polymers, like much better processability, good mechanical properties even with relatively low melt viscosities etc.

For example the two Patent Applications EP 3266824 A1 ed EP 3266825 A1 by Basell Poliolefine Italia, disclose the synthesis of isotactic metallocene butene-1 polymer compositions, that have a high Melt Flow Rate (and therefore a low molecular weight and melt viscosity) and a bimodal composition, directly obtained during polymerization, in two consecutive and separate reaction steps, where the first polymer (polymer A) of said compositionally bimodal polymer compositions is an isotactic butene-1 homopolymer or an isotactic butene-1 copolymer with another olefin, while the second polymer (polymer B) is an isotactic copolymer of butene-1, with another olefin, with a chemical composition obviously different from A).

Such unusual bimodal nature of these butene-1 polymer compositions, directly obtained in two separate steps of the polymerization, gives to these materials very peculiar and interesting characteristics especially for their use as components of hot-melt adhesives.

The Patent Application WO2018/007451A1 discloses hot-melt adhesive formulations comprising, as their main polymeric component, at least one isotactic metallocene butene-1 polymer composition at low viscosity, that has a bimodal composition, and that just corresponds to one of the butene-1 polymer compositions disclosed and claimed by Basell Poliolefine Italia in the two above mentioned Patent Applications.

For such formulations, said Patent Application WO2018/007451A1 claims novel and excellent properties regarding good adhesion, good cohesion and optimum processability, both for applications by Spraying and Fiberization and by Slot-Die coating, showing in particular that all those properties are totally different and substantially improved compared to all the analogous hot-melt adhesive formulations based on "old generation" polybutenes-1 from Ziegler-Natta catalysts that are described in all the previous Prior Art.

Said previous Prior Art, concerning adhesive formulations based on polybutenes-1 from Ziegler-Natta catalysts, is discussed in details in the above mentioned PCT Patent Application.

For the hot-melt adhesive formulations claimed by WO2018/007451A1, the inventors specify that they comprise, besides the above mentioned butene-1 polymer compositions, also from 5% by weight and 40% by weight of at least one viscosity modifier that is not solid at room temperature or of a blend thereof; and that preferably they contain between 8% by weight and 30% by weight of such viscosity modifier(s) or more preferably between 10% by weight and 20% by weight. I.e. all the hot-melt adhesive formulations disclosed in WO 2018007451A1 are to be considered highly plasticized by the use of large quantities of at least one viscosity modifier. In fact, all the Examples according to the invention that are disclosed in said Patent Application comprise 13% by weight of a viscosity modifier that is liquid at room temperature and that in the particular case is a paraffinic mineral oil. Moreover, the hot-melt adhesive formulations claimed in WO2018/007451A1 may comprise small quantities of waxes, not greater than 5% by weight, that are said to be used essentially for modifying the "Open Time" of the adhesive. However, about said generic additional waxes, the inventors or do not specify either their chemical nature or the molecular structure; or they state to prefer polypropylene waxes.

SUMMARY OF THE INVENTION

The problem that the present invention intends to solve is to formulate hot-melt adhesives that have unexpectedly good characteristics of very high adhesiveness and very high cohesion, which characteristics allow to utilize them in extremely critical and demanding uses, like some laminate structures inside hygienic absorbent articles, uses in which formulations already disclosed by the prior art and based on analogous polymeric systems, fail.

These novel and unexpectedly enhanced characteristics are obtained still keeping and even improving the most useful qualities of the previous formulations, like very low melt viscosity (in spite of the exceptionally small content of viscosity modifiers); optimum processability both in Spraying/Fiberization as well as in Slot-Die Extrusion/Coating; further increase during time of the adhesive, cohesive and rheological properties of the adhesives and of the relative bonded laminate structures, due to a slow crystallization, delayed in time, that occurs under room conditions.

A substantially improved additional quality, compared to the previously disclosed similar formulations, is also a much more precise and effective control of the very negative phenomenon called "bleed-through" (see later); as well as, as secondary but still important characteristics, a significant improvement or elimination of possible bad odors from the adhesive, and a practically full elimination of possible migrations/bleeding of low molecular weight compounds (essentially contained in most viscosity modifiers), migrations that may change during time even in an extremely negative way the adhesive properties of the formulations.

Said problems are solved by an adhesive composition having the characteristics of claim 1) and of claims from 29) to 33), by a bonded structure having the characteristics of claim 49), by an article having the characteristics of claims from 51) to 53). The other sub-claims disclose preferred embodiments.

DETAILED DESCRIPTION OF THE PREFERRED EMBODIMENTS AND MAIN PROPERTIES OF THE ADHESIVES ACCORDING TO THE PRESENT INVENTION

The Isotactic Metallocene Butene-1 Polymer Compositions at Low Viscosity and with a Bimodal Composition As said, the adhesive hot-melt formulations according to the present invention comprise, as their main polymeric component, at least one isotactic metallocene butene-1 polymer composition at low viscosity (and therefore at relatively low average molecular weight), and that has a substantially bimodal composition, directly obtained during polymerization, in two consecutive and separate reaction steps, where the first polymer (polymer A) of said compositionally bimodal polymer composition is an isotactic butene-1 homopolymer or an isotactic butene-1 copolymer with another olefin, while the second polymer (polymer B) is an isotactic copolymer of butene-1, with another olefin, with a chemical composition obviously different from A), qualitatively and/or quantitatively.

Said novel metallocene butene-1 polymer compositions are described in details, both as chemical and physical-chemical characteristics and as methods for their synthesis, in the two mentioned Patent Applications EP 3266824 A1 ed EP 3266825 A1, that, for such aspects are herein incorporated as a reference.

These aforesaid metallocene butene-1 polymer compositions (and the adhesive formulations that comprise them at relevant levels) show a very peculiar behavior during time that make their adhesive, mechanical and rheological properties substantially change, due to a slow and spontaneous crystallization under room conditions of the chains of polybutene-1. In particular these phenomena of slow and spontaneous crystallization, that on average complete in five days, are the reason why the adhesive formulations according to the present invention have an Elastic Modulus G' at five days that is remarkably greater than the same parameter measured at Time Zero; moreover they have a Tan Delta at five days that is remarkably smaller than their Tan Delta measured at Time Zero.

Said crystallization phenomena and the ensuing slow variation in time of the adhesive, mechanical and rheological properties of the above described metallocene butene-1 polymer compositions, with a bimodal composition, and of the adhesive formulation comprising them, are described in details in the already mentioned Patent Application WO2018/007451A1, that, just for what regards such aspects, is herein incorporated as a reference.

Each of said metallocene butene-1 polymer compositions can be concisely described as a butene-1 polymer composition, having a Melt Flow Rate (MFR), measured according to ISO 1133 at 190° C. and under a load of 2.16 kg, comprised between 200 and 6,000 g/10 minutes, and preferably between 400 and 5,000 g/10 minutes, that has a bimodal-type composition comprising:

A) a butene-1 homopolymer or a copolymer of butene-1 with one or more comonomers selected from ethylene and higher alpha-olefins with a number of Carbon atoms equal to three or greater than three, having a copolymerized comonomer content (CA) not greater than 5% by mole, preferably not greater than 4% by mole;

B) a copolymer of butene-1 with one or more comonomers selected from ethylene and higher alpha-olefins with a number of Carbon atoms equal to three or greater than three, having a copolymerized comonomer content (CB) of from 6% to 25% by mole, preferably from 8% to 20% by mole.

Said polymer composition has a total copolymerized comonomer content, referred to the total weight of A) and B), from 3% and 18% by mole, preferably from 5% to 15% by mole.

In a first embodiment of the present invention, said polymer composition has a content of fraction soluble in xylene at 0° C. not smaller than 65% by weight, and preferably not smaller than 70% by weight, said fraction soluble in xylene being determined on the total weight of A) and B).

In a second embodiment of the present invention, said polymer composition has a content of fraction soluble in xylene at 0° C. not greater than 60% by weight, and preferably not greater than 55% by weight, said fraction soluble in xylene being determined on the total weight of A) and B).

Said components A) and B) are preferably obtained directly in a polymerization consisting in two consecutive and separate reaction steps, therefore, the polymer composition described herein can be obtained directly in a polymerization even for what concerns global values of MFR that are sufficiently high (low viscosity), without requiring the use of peroxides or of other substances that generate free radicals, able to break polymeric chains to lower molecular weights.

In a first embodiment of the present invention, specific amounts of fraction soluble in xylene at 0° C. for the butene-1 polymer composition as provided herein, expressed as the weight content of fraction measured by extraction with xylene on the total weight of A) and B), range from 65% to 95% by weight, preferably from 70% to 90% by weight.

In a second embodiment of the present invention, specific amounts of fraction soluble in xylene at 0° C. for the butene-1 polymer composition as provided herein, expressed as the weight content of fraction measured by extraction with xylene on the total weight of A) and B), range from 35% to 60% by weight, preferably from 40% to 55% by weight.

When A) is a copolymer, a specific lower limit of comomomer content is of 1% by mole.

Preferably, when both A) and B) are copolymers, the difference between the percent values of the copolymerized comonomer contents of B) and A) satisfies the following relation:

$$(CB)-(CA) \geq 5; \text{ or } (CB)-(CA) \geq 6.$$

The relative amounts of components A) and B) can be easily determined depending upon the desired value of total copolymerized comonomer content, the comonomer contents of the single components and their content of fraction soluble in xylene at 0° C.

Preferred amounts, in the aforementioned first embodiment of the present invention, are from 10% to 40% by weight, and preferably from 15% to 35% by weight of A)

and from 60% to 90% by weight, preferably from 65% to 85% by weight of B), referred to the total weight of A) and B).

In the aforementioned second embodiment of the present invention, preferred amounts are from 35% to 65% by weight, and preferably from 40% to 60% by weight of A) and from 35% to 65% by weight, preferably from 40% to 60% by weight of B), referred to the total weight of A) and B).

Specific examples of higher alpha-olefins with a number of Carbon atoms equal to three or greater than three, that can be present as comonomers, in addition or in alternative to ethylene, in components A) and B) are alpha-olefins of formula CH2=CHR wherein R is methyl or an alkyl radical containing 3 to 8 or 3 to 6 Carbon atoms, such as propylene, hexene-1, octene-1. However, ethylene is the preferred comonomer, in particular for component B).

The present butene-1 polymer composition can have a measurable crystallinity even at Time Zero; while it certainly has a measurable crystallinity after aging at five days, a period of time in which a spontaneous crystallization at room temperature occurs and completes, with ensuing variations both of crystalline morphology as well as of the total quantity of crystallinity. In fact, as illustrated in details in the already mentioned references, the present butene-1 polymer compositions may form, even at Time Zero, during their solidification from the molten state, a relatively limited quantity of a crystalline form, having a tetragonal structure, called "Form II", a form that is thermodynamically unstable. During the slow, spontaneous crystallization in time, the initial crystals of said unstable form transform, in about five days, into the hexagonal form that is thermodynamically stable, called "Form I", while simultaneously also new crystals of Form I are created, in this way substantially increasing the overall crystallinity.

All the crystallinities of all the materials disclosed herein are identified and measured, in a DSC (Differential Scanning Calorimetry) diagram, through the presence of temperature-peaks of melting (or of crystallization) of the crystalline fractions, e.g. of polybutenes-1.

The DSC measurements, both in the crystallization cycles (i.e. in decrease of temperature) or in melting cycles (in increase of temperature) are performed by following the method ASTM D 3417-99; said cycles are performed between +180° C. and −70° C. (or vice versa) in order to have a complete information about all the phenomena occurring in the material, e.g. also for measuring its Glass Transition Temperature, Tg.

The Enthalpies of Crystallization or of Melting are expressed in J/g and are given by the area (obtained through integration) of the peak or by the sum of the areas of the possible multiple peaks that appear during a DSC cycle.

The DSC measurements on the butene-1 polymer compositions, and in general on all the single pure ingredients of the present adhesive formulations, are performed at temperature variation rate of 10° C./minute, as it is preferred by ASTM D 3417-99.

On the contrary, the DSC measurements on the hot-melt adhesive formulations of the present invention, are performed still according to the same Method but with a temperature variation rate equal to 1° C./minute. This modification of the method has been introduced because, especially in the Crystallization cycles, a cooling rate equal to 1° C./minute mimics very well the real phenomena that occur during the application on the substrate of the molten adhesive and its slow spontaneous cooling, setting and possible crystallization at the moment when the adhesive bond is formed.

In particular, even at Time Zero, the present metallocene butene-1 polymer composition, with a bimodal composition, can show a certain level of crystallinity measured e.g. through the presence of one of more melting peaks, in a DSC heating cycle between −70° C. e+180° C., cycle that (by definition of Time Zero) is performed at the upmost within 180 minutes since its setting from the molten state. If said melting peaks at Time Zero are present, they generally are located at temperatures not higher than 110° C., mainly between about 75° C. and about 110° C. They are just ascribed to the melting of the crystalline Form II of the polybutenes-1 (Tm II) and the area below said peaks is taken as a measure of the relative overall melting Enthalpy (Delta H TmII). In case that more than one melting peak is present, the peak corresponding to the highest temperature is taken as Tm II.

More specifically, the metallocene butene-1 polymer composition, with a bimodal composition, used in the adhesive formulations of the present invention, has an overall melting Enthalpy Delta H Tm II not greater than 20 J/g, preferably from 1 J/g to 20 J/g, when measured with a temperature increase rate of 10° C./minute.

Moreover, in a DSC heating cycle performed after the aging of the material at room temperature for five days, the present metallocene butene-1 polymer composition shows one or more melting peaks, that generally are located at temperatures not higher than 110° C., especially between 30° C. and 110° C. Said peak or peaks at five days are ascribed to the melting of the crystalline Form I of polybutene-1 (Tm I) and the area below said peak or peaks is taken as a measure of the relative overall melting Enthalpy (Delta H Tm I). In case that more than one melting peak is present, the peak corresponding to the highest temperature is taken as Tm I.

More specifically, the metallocene butene-1 polymer composition, used in the adhesive formulations of the present invention, has an overall melting Enthalpy Delta H TmI not greater than 50 J/g, preferably from 3 J/g to 50 J/g, or from 5 J/g to 50 J/g, when measured with a temperature increase rate of 10° C./minute.

Without being linked to any theory, because the crystals of the stable hexagonal crystalline form of polybutene-1 (Form I), measured at five days, are the ones that optimize at the best the final adhesive and mechanical properties of the hot-melt adhesive formulations of the present invention, it is preferable that Tm I, measured as described above, is rather high; in particular it is preferable that Tm I is not lower than 60° C. and more preferably not lower than 80° C.

The preferred and above specified values of overall MFR of the metallocene butene-1 polymer composition, with a bimodal composition, that is comprised into the adhesive formulations of the present invention, can be obtained by combining in opportune ratios, the components A) and B) that theoretically may have individual MFR's of whatever value. Practically however, the metallocene butene-1 polymer composition, with a bimodal composition, preferred in the present invention, have also the individual MFR's of the two components A) and B) that are sufficiently high, in particular within the range from 200 and 6,000 g/10 minutes and preferably from 400 and 5,000 g/10 minutes.

Following a traditional technical habit, in the field of hot-melt adhesives, the viscosity in the molten state both of the final adhesives as well as of their components, is often measured through the so called "Brookfield viscosity" according to the Method ASTM D 3236-73.

Under this aspect, the metallocene butene-1 polymer compositions, with a bimodal composition, comprised in the adhesives of the present invention, have a Brookfield viscosity, measured at 190° C., between 1,000 and 50,000 mPa·s, more preferably between 2,000 and 30,000 mPa·s.

Moreover, said isotactic metallocene butene-1 polymer compositions, comprised in the adhesive formulations of the present invention, show at least one of the following further characteristics:

An overall (i.e. measured by GPC on the final composition of the two components A and B) Polydispersity Index PDI=Mw/Mn, where Mw is the Mass Average Molecular Weight and Mn is the Number Average Molecular Weight, that is equal or lower than 4, preferably lower than 3, more preferably lower than 2.5, being in any case the lower limit equal to 1.5;

A Polydispersity Index of the single components A or B preferably not greater than 2.5;

An Mw not lower than 5,000 and preferably comprised between 10,000 and 100,000;

An Intrinsic Viscosity measured in Tetra-hydronaphthalene (THN) at 135° C., not greater than 0.6 dl/g, preferably comprised between 0.1 and 0.6 dl/g, and more preferably comprised between 0.2 and 0.6 dl/g;

Isotactic pentads (mmmmm) measured by 13C-NMR operating at 150.91 MHz, greater than 90%, preferably greater than 93% and more preferably greater than 95%;

4,1 insertions not detectable by 13C-NMR operating at 150.91 MHz;

A Yellowness Index, measured according ASTM D 1925, not higher than zero, preferably comprised between zero and −10, more preferably comprised between −1 and −9 and even more preferably comprised between −1 and −5;

A D Shore Hardness value not greater than 50, preferably not greater than 45, in particular comprised between 15 and 50, and preferably comprised between 15 and 45;

A Stress at Break, according to ISO 527, comprised between 1 MPa and 25 MPa, preferably comprised between 1 MPa and 20 MPa;

An Elongation at Break, according to ISO 527, comprised between 100% and 1,500%, and preferably comprised between 450% and 1,000%;

A Glass Transition Temperature, measured by DSC, comprised between −35° C. and −10° C.;

A density at room temperature not lower than 0.875 g/cm$^3$, preferably comprised between 0.875 g/cm$^3$ and 0.92 g/cm$^3$, more preferably comprised between 0.88 g/cm$^3$ and 0.91 g/cm$^3$.

Isotactic metallocene butene-1 polymer compositions, with a bimodal composition, corresponding to the ones described above, are for example manufactured and marketed by LyondellBasell with the trade mark Koattro PB M, like Koattro PB M 0600M, Koattro PB M 1500M, Koattro PB M 2500M and so on.

The hot-melt adhesive formulations of the present invention comprise between 10% by weight and 99.5% by weight, preferably between 25% by weight and 90% by weight, more preferably between 30% by weight and 70% by weight, of at least one isotactic metallocene butene-1 polymer composition, that has a low viscosity and that has a substantially bimodal composition, as above described.

The Viscosity Modifiers Not Solid at Room Temperature

The hot-melt adhesive formulations according to the present invention comprise, besides at least one butene-1 polymer composition, as above described, also a very small quantity (see below) of at least one viscosity modifier or of a blend of viscosity modifiers that is/are "not solid" at room temperature, according to the meaning previously defined for such expression.

However differently from what previously disclosed and claimed, e.g. in the already mentioned Patent Application WO2018/007451A1 and contrary to what disclosed also in all the previous Prior Art, the hot-melt adhesive formulations disclosed and claimed herein, comprise an unusually small quantity, i.e. less than 5% by weight, of said viscosity modifiers that are not solid at room temperature.

As it is well known to the averagely expert person in the technology of formulating hot-melt adhesives, the great majority of these adhesive formulations normally contain large quantities of one or more viscosity modifiers, that generally have a very low molecular weight and are liquid at room temperature.

The scope for the addition of such additives is just to significantly modify the melt viscosity of the final formulation, in most cases decreasing it to much lower values than the melt viscosities of the sole molten polymers, present in the formulation. Such substantial decreases in viscosity make easier a good processability of the hot-melt adhesives and make it possible to apply them at relatively low temperatures (e.g. generally not higher than 180° C. and often much lower) so that not only to save energy is possible, but it is also possible to apply said adhesives even on very thin and thermo-sensitive substrates, like the plastic films and nonwovens largely used in hygienic absorbent articles, substrates that would be destroyed or unacceptably deformed by the contact with hot-melt adhesives at temperatures higher than 180° C.

The same averagely expert persons in the technology of formulating hot-melt adhesives also know very well the positive and negative effects that, on the general properties of an adhesive, has the fact of varying in one direction or the other, decreasing or increasing it, the content of such viscosity modifiers, in the technology sometimes also called "plasticizers" or "fluidizers".

Before entering in such a discussion, it is worthy to recall that for all adhesives, according to the fundamental criteria of the Science of Adhesion, the achievement of "optimum" performances in an adhesive is closely linked to a precise and accurate balance between its adhesive properties and its cohesive properties.

In all cases, the "overall adhesive strength" of an adhesive, i.e. the strength needed for breaking a certain bond between the adhesive and a substrate, is the sum of two families of different contributions, that can be defined as "purely adhesive" and as "purely cohesive". The first ones are generated by the chemical and physical-chemical interactions (van der Waals forces, molecular dipole forces, Hydrogen bonds etc.) that are established at distances of the same order of magnitude of molecular dimensions, between the molecules of the adhesive and the ones of the substrate; therefore these forces are strongly dependent on the chemical nature of the materials as well as on the "ease" by which the adhesive intimately contacts the substrate (or as it is said in technical jargon, on how it "wets" the substrate). Moreover, their contribution is directly proportional to the "wetted" area of the substrate, i.e. to the real area of contact between the adhesive and the substrate. As it is not only rigorously demonstrated by the Science of Adhesion, but as it is also intuitive, the "wetting" by an adhesive of larger areas of the substrate, and therefore the possibility of creating strong "purely adhesive" interactions, are facilitated also by its "softness" and "tackiness".

The second family of contributions to the overall adhesive strength, i.e. the cohesive contributions, are on the contrary proportional to the cohesion of the adhesive, i.e. to its "intrinsic mechanical resistance"; or also, said in another way, to the strength needed to "physically break" the film of adhesive that is present inside a certain bonded structure.

Any generic adhesive bond fails when the applied strength exceeds the sum of the "purely adhesive" strengths and of the "purely cohesive" strengths of the used adhesive. If the first kind of strengths prevail, it is said that a certain adhesive fails for a "prevalently adhesive" failure; in the opposite case, it is said that it fails for a "prevalently cohesive" failure.

Too hard adhesives will have optimum cohesion, but they will show on the contrary exceedingly low "purely adhesive" contributions, because a hard adhesive is not sufficiently "soft and tacky" to wet in a sufficient way the substrate. On the contrary, too soft and tacky adhesives will have high adhesiveness, but they will easily fail because of a cohesive failure. In both cases, the observed overall adhesive strength will be unacceptably low. It is therefore clear that an optimization and a maximization of the overall adhesive strength of a generic adhesive, necessarily requires an optimization, maximization and balance of both the adhesive and cohesive components of the adhesion.

Returning to the consequences that, in a hot-melt adhesive, derive from the fact of increasing or decreasing the content of viscosity modifiers, it is well known that, by decreasing the level of such additives (that often are fluids at low or very low molecular weight) it is possible to observe an increase in the mechanical properties of the adhesive formulation. This mechanical strengthening of the adhesive is expressed by a significant increase (both in the solid and molten state) of its parameter Elastic Modulus G'. This is also reflected in a significant increase of its Tension Modulus i.e. of the difficulty of "mechanically breaking" the adhesive; in other words, we can observe a significant increase of the cohesion of the adhesive. This may seem a positive effect, but actually this is not true. As it is well known to every person averagely skilled in Rheology, to increase the Elastic Modulus G' means also to make the adhesive "harder", and therefore less tacky, impairing in this way its purely adhesive properties. Hence the action of significantly decreasing the levels of viscosity modifiers that are present in a hot-melt adhesive, means to make the formulations much less tacky and adhesive, besides the obvious fact of considerably increasing their melt viscosity, substantially worsening their processability and obliging the user to apply them at higher temperatures, at the limit excessively high.

It is just for all these reasons that, as known to every person averagely expert in the technology of formulation of hot-melt adhesives, in the great majority of such formulations the added levels of viscosity modifiers are generally rather high.

And just according to these criteria, using as the polymeric base the same isotactic metallocene butene-1 polymer compositions, described above and that are used also in the present invention, e.g. the inventors of the already mentioned Patent Application WO2018/007451A1 claim a content of viscosity modifiers that is comprised between a minimum of 5% by weight and a maximum of 40% by weight. Actually, said invention prefers for these additives much higher levels, comprised between 8% by weight and 30% by weight, and even better between 10% by weight and 20% by weight. In fact, all the Examples according to that invention, shown in said Patent Application, actually contain 13% of a viscosity modifier at low molecular weight.

Contrary to what hence taught by the prior art and in particular by the mentioned Patent Application WO2018/007451A1, according to the present invention, it has surprisingly been discovered that, by utilizing the above described novel isotactic metallocene butene-1 polymer compositions, at low viscosity and with a substantially bimodal composition, with a narrow bimodal distribution both as chemical composition and as molecular weights, the usual massive addition of viscosity modifiers is not only unneeded, for improving the adhesiveness and the processability of the formulations of the present invention, but can even have negative effects on an optimum balance and on an increase to significantly higher values (compared to what can be obtained with the known high quantities of these additives) of the values of adhesiveness and cohesion of the present adhesive formulations.

Therefore the hot-melt adhesive formulations according to the present invention comprise substantially lower quantities of a viscosity modifier or of a blend of viscosity modifiers, that are not solid at room temperature, compared to what taught by all the previous prior art, dealing with hot-melt adhesives based on polybutene-1, and in particular compared to what taught by the already mentioned Patent Application WO2018/007451A1. More specifically the hot-melt adhesive formulations according to the present invention comprise less than 5% by weight of a viscosity modifier or of a blend of viscosity modifiers, that are not solid at room temperature, and preferably comprise not more than 4.5% by weight of said viscosity modifier or of a blend of viscosity modifiers, not solid at room temperature.

Such exceptionally small levels of viscosity modifiers are unexpectedly associated with an unpredictable increase and with an optimum balance of the adhesive and cohesive properties of the formulations disclosed herein, so much that they are able to satisfy and withstand particularly critical and demanding uses, in which analogous adhesives, formulated according to the prior art with much higher levels of viscosity modifiers, fail.

Even more surprisingly it has been also discovered that the adhesives disclosed in the present invention, in spite of their exceptionally small content of viscosity modifiers, keep low melt viscosities and an excellent processability, even in processes at high or very high applied "shear rate", like Spraying and Fiberization as well as Slot Die Coating, and even on industrial lines that operate at high speed, e.g. at 250 m/minute or higher.

Moreover, the decrease to unusually low levels of the content of viscosity modifiers in the present adhesive formulations, allows to achieve additional characteristics that are very beneficial, compared to the standard hot-melt adhesives with a much higher content of these additives at low molecular weight. In particular:

the viscosity modifiers almost always contain fractions at very low molecular weight, that have a not negligible volatility even at room temperature. This often gives to these materials a characteristic and unpleasant odor that must be absolutely avoided, especially in hygienic absorbent articles;

the above mentioned fractions at very low molecular weight may, during time, slowly migrate outside the adhesive itself, causing a phenomenon of bleeding. If this occurs, very negative consequences thereof may be not only an unacceptable variation and degradation over time of the properties of the adhesive, but also, if these bled substances come in contact with the skin of the user, they can cause serious problems of skin irritation, sensitization/allergic reactions and even toxic effects.

Hence, to decrease as much as possible the quantity of viscosity modifiers added to the adhesive formulations, can be only a highly positive and desirable fact, especially if a high adhesion and cohesion and a low viscosity are maintained.

More specifically the adhesive formulations according to the present invention have a Brookfield viscosity, measured at the temperature of 170° C., that is not greater than 30,000 mPa·s, preferably not greater than 15,000 mPa·s, more preferably not greater than 10,000 mPa·s and even more preferably not greater than 5,000 mPa·s.

In an embodiment of the present invention, the herein disclosed hot-melt adhesive formulations have a sufficiently low viscosity even at temperatures significantly below the above mentioned 170° C., so that they can be optimally processed and applied on a substrate, both by spraying and slot-die coating technologies, even at temperatures not higher than 145° C., preferably not higher than 140° C. and even more preferably at temperatures not higher than 135° C.

This particular group of formulations according to the present invention, that are processable and applicable even at unusually low temperatures, show a Brookfield viscosity, measured at 130° C., that is not greater than 15,000 mPa·s, preferably not greater than 12,000 mPa·s and even more preferably not greater than 10,000 mPa·s.

The viscosity modifier(s), that is/are not solid at room temperature, and that are comprised, at a level lower than 5% by weight in the adhesive formulations of the present invention, comprise e.g. paraffinic mineral oils; naphthenic mineral oils; paraffinic and naphthenic hydrocarbons not solid at room temperature, and their blends; oligomers, that are not solid at room temperature, of polyolefins and of their copolymers, like not solid at room temperature oligomers derived from ethylene, propylene, butene, iso-butylene, their copolymers and the like; plasticizers that are not solid at room temperature formed by esters like phthalates, benzoates, sebacates; vegetable oils; natural and synthetic fats; and their blends. Mineral oils and fats, both paraffinic and naphthenic, and their blends, are particularly preferred. Equally preferred are non-solid oligomers of polyolefins, synthesized through metallocene catalysts, and that have a specially low Polydispersity Index Mw/Mn, not higher than 2, preferably not higher than 1.8 and more preferably not higher than 1.5, like the metallocene poly-alpha-olefin oils (PAO) marketed by Exxon Mobil with the trade marks Spectrasyn and Elevast and the oligomeric copolymers propylene-ethylene, not solid at room temperature, marketed by Clariant with trade marks like Licocene PPA 330.

The Optimum Adhesive and Cohesive Properties of the Claimed Formulations and Their Peculiar Stress-Strain Curve As already mentioned, in spite of their low melt viscosities, the adhesive formulations according to the present invention show an exceptionally good balance between high adhesiveness and high cohesion, that allows them to successfully pass particularly critical tests that simultaneously challenge both the adhesiveness and the cohesion of an adhesive and in which other similar formulations, formulated according to the teachings of the prior art, fail.

A test method that simultaneously challenges, in particularly severe conditions, both the adhesive and cohesive properties of an adhesive, is the so called "Hang Test" or "Hang Time Test" (vide infra for a detailed description). It mimics very well the very critical conditions, of very high stress, even more applied according to angles that vary in time, in which the adhesives work inside laminate bonded structures, formed e.g. by a plastic film and a nonwoven, when said laminates are utilized in particularly demanding uses, like e.g. the external impermeable backsheet of a baby or adult-incontinent diaper.

It has also been discovered that, besides by the mentioned Hang Test, the unexpectedly good and improved properties of the present adhesive formulations, both as very high adhesion and cohesion, can be detected also by the fully peculiar form shown by their curve of Stress-Strain to break, in a tension test according to the previously described method.

In fact, by testing in parallel, samples of various formulations both in the Hang Test and in tension tests to break, it is observed that the two types of test are somehow very well correlated; therefore, it is possible to predict the possible resistance of a laminate structure in use (a situation that is well mimicked, measured and predicted by the Hang Test) also through particular values of some parameters in the Stress-Strain to break curve of the adhesive under test.

More specifically: too "soft" adhesives and hence (as already seen) that fail both in real use and in the Hang Test mainly for their insufficient cohesion (cohesive failure of the bond) show Stress-Strain to break curves with a very low peak/ultimate tensile strength and with also a very low elongation. In fact, the peak of the curve is proportional to the Elastic Modulus G' of the material, and if the material is very "soft" the parameter G' is low; as it is equally low the elongation to break, because the material, having low cohesion, physically ruptures even under a very limited stress. Therefore, for insufficiently cohesive adhesive, the area under the curve Stress-Strain to break, is small. This is perfectly logical because, as the Mechanical Science teaches, the area under the curve Stress-Strain to break is the so called "toughness" of a material and represents the amount of energy per unit volume that a material can absorb, by plastically deforming/stretching, before rupturing. A low cohesion is hence equivalent to a low toughness, and to a small area under the Stress-Strain to break curve. Said area (and so the toughness of a material) has the physical dimensions expressed as $J/m^3$ or as $MJ/m^3$.

On the contrary, adhesives that fail because they are too "hard" and that therefore, as seen, fail for insufficient adhesion (adhesive failure of the bond) show Stress-Strain curves with an excessively high peak, as obvious because their high hardness is expressed by a high value of their Elastic Modulus G' (and hence of the stress at the peak). The area under the curve, and therefore the toughness of the material, may be relatively large; but this is not beneficial to the strength and integrity of the adhesive bond, because the film of adhesive can easily rupture, at low elongations, because of its excessive hardness and fragility, even under very limited deformations (hence, as a consequence of even very small "movements" of the laminate structure during use).

It is therefore clear that, in order to have an overall adhesive strength that is particularly high, an overall strength formed by the balanced combination of a high adhesiveness and of a high cohesion, so that the adhesive can pass even the Hang Test, it is necessary also that the Stress-Strain to break curve of the adhesive under test shows at the same time the following three properties:

a) A large area under said curve and hence a large toughness/cohesion (i.e. the toughness of the adhesive is >than a certain minimum value)

but at the same time, it is also needed that:
  b) The peak of maximum stress of the curve (or "Ultimate Tensile Strength") and the value of the Elastic Modulus G' of the adhesive (that are mutually proportional) are comprised between two values, a lowest and a highest value (i.e. the adhesive is sufficiently soft and tacky, but it is neither too "soft" nor too hard and fragile);
  c) The elongation at break of the adhesive exceeds a certain minimum value (i.e. again the adhesive is not too hard and fragile).

Obviously, because all the properties of the present formulations significantly vary with time, after that they are applied from the melt, due to the peculiar spontaneous slow crystallization of the butene-1 composition, crystallization that occurs at room temperature and completes in about five days, all the above mentioned mechanical and rheological parameters, measured both on the adhesives themselves (rheological parameters and Stress-Strain curve) and on the laminate structures containing said adhesives (e.g. Hang Time test), are performed at room conditions on samples that have been aged for five days, at 23° C. and 50% Relative Humidity, so to perfectly mimic the properties that will be tested in the real use by a user of hygienic absorbent articles containing said adhesives.

For emphasizing also the substantial increase observed during aging in the rheological, cohesive and adhesive properties of the particular adhesive formulations of the present invention, as a comparison, the same tests may also be performed at Time Zero, i.e., as previously defined, within a period of time not longer than 180 minutes since the moment in which the adhesive has set/solidified from the molten state, and since the laminate structure has been produced.

Returning to the peculiar shape of the of the Stress-Strain curve showed by the hot-melt adhesive formulations of the present invention, it has been discovered that such adhesives have, at the temperature of 23° C. and after an aging at room temperature for five days, Stress-Strain to break curves that satisfy the following conditions:
  An area under the curve Stress-Strain to break (Toughness) not lower than 0.2 $MJ/m^3$, and preferably not lower than 0.4 $MJ/m^3$;
  An Elongation at Break not lower than 200%, and preferably not lower than 250%;
  A maximum stress (i.e. the peak of the Stress-Strain curve or Ultimate Tensile Strength) comprised between 0.15 MPa and 1.5 MPa, preferably comprised between 0.20 MPa and 1.2 MPa and more preferably comprised between 0.25 MPa and 1.0 MPa;
or, as an alternative to the latest point:
  An Elastic Modulus G', measured at 23° C. and 1 Hz, comprised between 3.0 MPa and 25.0 MPa, and preferably comprised between 5.0 MPa and 20.0 MPa;

The excellent combination of adhesive and cohesive strengths of these hot-melt formulations, even in bonded structures comprising at least one fibrous or perforated substrate, are properly measured, in a direct way and in a particularly severe situation, as already said, by the experimental method called "Hang Test" or "Hang Time Test" that will be illustrated later.

Other Components of the Hot-Melt Adhesives According to the Present Invention

Waxes with a Peculiar Chemical Composition and Structure

In an embodiment of the present invention, the hot-melt adhesive formulations disclosed herein, also comprise less than 5% by weight of a wax or of a blend of waxes, preferably said wax or blend of waxes being formed by polyethylene waxes, that, even more preferably, are characterized by a highly linear/non-branched structure and by a Polydispersity Index unusually small (see later for more details).

The present embodiment derives from the fact that, inside all hygienic absorbent articles, are present laminate bonded structures in which at least one substrate (but sometimes both) has holes, cavities, or is a fibrous substrate, for example a nonwoven bonded to a plastic film, or two bonded nonwovens or a nonwoven bonded to a woven cellulose/cotton fabric, and so on.

As always, also in these cases it is indispensable to assure a very high adhesion and cohesion (as e.g. measured by passing the Hang Time Test); but it is also indispensable to avoid a further very negative possible phenomenon that in the adhesive technology is known with the name of "Bleed Through" (see later for more details).

The already mentioned Patent Application WO2018/007451A1 was already claiming the possible presence, in the adhesives disclosed therein, of small quantities of waxes, not greater than 5% by weight. The stated scope for the addition of these small quantities of waxes was to tune the Open Time of the adhesive.

However, said Patent Application, in claiming the presence of a small level of a generic wax, did not specify and did not require for said waxes any particular characteristic, both about their chemical composition and chemical structure. The inventors limited themselves to later stating that, among all waxes, polypropylene waxes were particularly preferred, and even better the polypropylene waxes modified with maleic anhydride and having a softening point not lower than 120° C.

The preference for modified polypropylene waxes with a rather high softening point, can be understood for at least three reasons:
  Waxes with very high softening point (and hence also a very high setting point) are the most effective in shortening the Open Time of an adhesive, when it is considered too long;
  Especially waxes modified with maleic anhydride are well known, in the technology of hot-melt adhesives, as additives able to favor the wetting of the substrates and therefore are able to favor in general a high adhesiveness;
  It is reasonable to think that this special preference of WO 2018007451A1 for polypropylene waxes derives from the fact that Polybutene-1 and Polypropylene are highly compatible and fully miscible (see e.g. the article "The Polymer-Polymer Interaction Parameter in Polybutene-1/Polypropylene Blends" published in "Journal of Polymer Research" Vol. 3, No. 4, 235-238, October 1996, article that is herein incorporated as a reference). It is therefore reasonable to suppose that the intention of WO 2018/007451A1 was to maximize the compatibility and the perfect miscibility of these additives into the adhesive formulation by just preferentially using polypropylene waxes, that are highly compatible in such adhesives based on Polybutene-1.

Contrary to the criteria used by WO2018/007451A1 in selecting the most suitable waxes to be added into those adhesive formulations, the inventors of the present invention have surprisingly found that the addition (in any cases always in small quantities, lower than 5% by weight) of polyethylene waxes, especially if they have certain peculiar characteristics of molecular structure, unexpectedly gives to the hot-melt adhesive formulations of the present invention also the ability of controlling and avoiding the "Bleed Through" phenomenon, even in all the applications in which said phenomenon is particularly critical, at the same time obviously keeping an excellent and surprisingly improved balance between high adhesion and high cohesion, as shown by the passing of the Hang Time Test.

The switch between polypropylene waxes (preferred by WO2018/007451A1) and polyethylene waxes (preferred by the present invention) is not an obvious and intuitive switch, especially by considering the enormous difference in compatibility/miscibility that the common base polymer Polybutene-1 shows, from one side, with Polypropylene waxes, and, from the other side, with Polyethylene ones.

In fact, while, as said above, Polybutene-1 and Polypropylene are fully compatible and miscible, the behavior of the system Polybutene-1 and Polyethylene is just the opposite. In fact, these two latest polymers are highly incompatible and, if they are mixed in the molten state, they rapidly demix and then crystallize in two fully separate phases (see e.g. the article "Crystallization behavior of polyethylene and i-polybutene-1 blends" published in "Polymer" Vol. 27, No. 3, 337-343, March 1986, article that is herein incorporated as a reference).

Hence the fact that it is possible to observe in the present hot-melt adhesives, based on Polybutene-1, significant effects and, what's more, even very positive effects, by the addition of highly incompatible waxes, like the polyethylene waxes, is actually a fully unexpected and surprising finding; and in fact said waxes are never utilized as additives into adhesives based on Polybutene-1, both in all the relative patent prior art we are aware of, as well as in the current industrial practice, just because they are rightly considered as fully incompatible and immiscible with the base polymer.

On the contrary, the inventors of the present invention have unexpectedly found that the addition, in an overall quantity lower that 5% by weight, of at least one polyethylene wax or of a blend of two or more polyethylene waxes, especially if they have certain peculiar characteristics of molecular structure (see later), even if said waxes are chemically incompatible with the base polymer Polybutene-1, is just able to control and stop, with a surprising effectiveness, the very negative phenomenon known, in the technology of adhesives, with the name of "Bleed Through" (see later). And this aim is achieved without that these polyethylene waxes (also for their very low level of addition) may interfere, through their high crystallinity, with the main mechanism of crystallization, delayed in time, of the isotactic metallocene butene-1 compositions that are comprised in the present adhesives.

On the contrary, waxes that are highly compatible with the butene-1 polymer compositions, like polypropylene waxes, preferred and claimed by WO2018/007451A1, are completely ineffective in controlling and stopping the "Bleed Through" phenomenon in the present adhesive formulations.

In particular it has been observed that, among polyethylene waxes, that are in general surprisingly effective in controlling and stopping the Bleed Through" phenomenon, polyethylene waxes with an average Number Molecular Weight Mn not greater than 3,000 are even more effective and hence to be preferred. Even more preferred are waxes having a very small Polydispersity Index Mw/Mn (i.e. a very narrow distribution of molecular weights), especially those waxes having Mw/Mn not higher than 2.5, preferably not higher than 2.0 and even more preferably not higher than 2.5.

Preferred in a special way are for example the polyethylene waxes, having a fully linear structure, and an exceptionally small Polydispersity Index, comprised between 1.08 and 1.1, manufactured and marketed by Baker Hughes (USA) under the trade mark Polywax.

As said, a polyethylene wax or a blend of polyethylene waxes, may be present in the adhesive formulations of the present invention, in a quantity lower than 5% by weight and preferably not higher than 3% by weight.

Other non-polyethylene waxes, e.g. polypropylene waxes, especially if modified with maleic anhydride, even if they are fully ineffective in controlling and stopping the "Bleed Through", may be optionally added, for example for favoring the wetting of the substrates. Their percent level is anyhow not greater that 3% by weight and, in case also polyethylene waxes are present, the overall level of all the present waxes is anyhow lower than 5% by weight.

Description of the Bleed Through Phenomenon and its Measurement

The phenomenon known as Bleed Through can be defined and described in the following way. In many industrial technologies that utilize hot-melt adhesives, quite often at least one of the two substrates that are bonded (or in more critical cases, both substrates) has/have holes, cavities or voids. In particular, in the field of hygienic absorbent articles, various and different substrates having holes, cavities or voids, like fibrous substrates, as nonwovens; perforated plastic films, with holes having a bidimensional or tridimensional structure; microporous plastic films and so on are often used.

When a molten adhesive in applied on one of these fibrous or perforated substrates, the adhesive sets and bonds the substrate(s) by slowly cooling and solidifying. During this slow spontaneous cooling and setting of the molten adhesive, the adhesive bonds not just by "wetting" the substrate's surface (in the special meaning given to the verb "to wet" in the Science of Adhesion, i.e. to enter into a very intimate contact) but also by partially penetrating inside the holes, cavities and spaces of the substrates (for example, by partially penetrating between the fibers, if the substrate is a fibrous substrate etc.). Said partial penetration of the molten or semi-molten adhesive inside the holes or cavities of the fibrous or perforated substrate, is per se a positive phenomenon. In fact, thanks thereto, the overall adhesive strength of the final bond will be increased, because, besides the "purely adhesive" interaction between the surface of the adhesive and the surface of the substrate, in these cases there will be also a true "mechanical interlocking" between a fraction of the adhesive and the holes or fibers of the substrate.

It is also worthy to notice that it is anyhow suitable and beneficial to strengthen an adhesive bond on said fibrous or perforated substrates, by favoring a partial penetration of the adhesive itself inside their holes, cavities, voids or spaces. In fact a fibrous substrate or a perforated plastic film may have, just for the presence of the holes of for their fibrous structure, an actual area, available for the contact with the adhesive, that may be less than 50% of the overall geometrical area of the substrate itself. And because it is well known that, in all adhesive bonds, the "purely adhesive" contribution to the overall adhesive strength is directly proportional to the actual area of contact between the adhesive and the substrate, it is clear that it would be exceedingly difficult to strongly bond, by "pure adhesive interactions", said fibrous and perforated substrates that have a significantly reduced contact area for the adhesive; unless one can simultaneously favor a partial penetration inside the holes and spaces of the substrate, in this way creating also a robust mechanical interlocking between the adhesive and the substrate.

It is therefore advisable and beneficial that, when it is necessary to bond structures in which at least one of the two substrates has holes, cavities or voids, the most suitable hot-melt adhesives are the ones that, during their application from the melt and their subsequent setting, are also able to partially penetrate inside said holes, cavities, voids or spaces etc.

However, if this penetration is not just "partial", i.e. if the molten or semi-molten adhesive, because of its particular thermal and rheological properties, is unable to set and harden rather quickly, and therefore if it "does not stop" rather quickly in its penetration into the holes or between the fibers, it may happen that a significant fraction of this semi-molten adhesive continues to penetrate inside the fibrous or perforated substrate, being even able to emerge in a substantial quantity on the opposite external side of the substrate.

This behavior, that is just known in the hot-melt adhesive technology with the name of "Bleed Through", is an extremely negative phenomenon that absolutely needs to be stopped and avoided, both during the industrial manufacturing of bonded structures, where the Bleed Through might contaminate with adhesive's traces the production lines themselves; as well as inside and during the use of the final articles containing the adhesive. In fact, in this latest case, if the Bleed Through is present in any of the bonded structures inside the article, it may happen that said structures inconveniently adhere to other parts of the same articles to which they should not adhere; or it may happen that said structures are felt as irritatingly tacky on the skin of the final user, etc.

Obviously, said need to avoid Bleed Through of hot-melt adhesives, inside bonded structures, becomes even more difficult and critical when, as it often happens in the bonded structures used in hygienic absorbent articles, not only one, but both substrates have holes, cavities or voids, e.g. two bonded nonwovens, a nonwoven bonded to a cellulose/cotton fabric and so on.

The criticality of such phenomenon and the difficulty in avoiding it (anyhow assuring, as said, an optimum Hang Time, and hence a partial penetration of the adhesive inside the holes or between the fibers) is even more evident when we consider that those substrates, used inside hygienic absorbent articles, are always extremely thin, mostly thinner than 25 microns and often even thinner than 15 microns.

Therefore, summarizing the illustrated concepts, we can state that:

In the bonding of structures, in which at least one of the two substrates has holes, cavities, spaces etc., like fibrous substrates, perforated plastic films and so on, it is advisable (and often indispensable) to make sure that the adhesive, during its application and setting from the melt, is able to flow and partially penetrate inside the holes or between the fibers of the substrate. If this doesn't occur, i.e. if the adhesive solidifies too quickly and so there is no penetration or only an insufficient penetration, there will be in general an unacceptably low adhesion on this kind of substrates, because their actual area for the contact between adhesive and substrate is strongly reduced (frequently by about 50% or more) just because of the presence of the holes or because of the fibrous structure.

If, on the contrary, around its temperature of application and setting, an adhesive tends to remain semi-fluid for a too long time, and therefore it continues to flow and to penetrate inside the fibrous or perforated substrates, it can occur the very negative phenomenon called "Bleed Through", when a significant fraction of the adhesive even goes across the whole perforated or fibrous substrate(s) and emerges on the other side.

Obviously, as every person averagely skilled in Rheology well knows, this ability of the adhesive of stopping in a sufficiently quick way (but not too quickly!) around its setting point; or vice versa, of setting in a too slow way, continuing to flow in a semi-fluid state (in this way causing the Bleed Through), depends on its Rheological Setting Temperature, Tx, and on the value at that temperature of its main rheological parameters. In particular, it depends on the value (an identical value, by definition of Tx) that the Elastic Modulus G' and the Viscous Modulus G" have at that temperature, value that is generally called the Crossover Modulus and represented with the symbol Gc.

As it can be demonstrated also in a rigorous way, it is anyhow also quite intuitive the way in which the two parameters Tx and Gc control the ability of the semi-molten adhesive of flowing for a longer or shorter time, and hence of penetrating more or less deeply inside the holes and spaces of a fibrous or perforated substrate. Because the rate at which a hot-melt adhesive, coated in the molten state, spontaneously cools, can be considered as practically constant (given a certain application process), it is clear, for example, that the lower is its Rheological Setting Temperature, Tx, the longer is the time that the molten adhesive has, before its setting, for spontaneously flowing and penetrating inside possible holes and spaces of a substrate. Moreover, as it is well known to any person averagely expert in Rheology, the absolute value of the Crossover Modulus Gc (i.e. the absolute value of the two rheological Moduli at the Setting Point Tx) is directly proportional e.g. to the viscosity of the semi-molten adhesive at that temperature; then, even at parity of Tx between two different adhesives, if Gc is too low, this could anyhow cause Bleed Through.

Obviously these considerations are valid also because it is necessary to take into account the existence also of upper limits for such parameters, because, as seen, it is anyhow advisable, for maximizing the adhesion on fibrous or perforated substrates, to favor a partial penetration of the semi-molten adhesive inside said holes or between the fibers. Therefore, if the setting temperature Tx is too high or if, at that temperature, the absolute value of Gc is too high, the semi-molten adhesive would solidify too quickly, or it would be too viscous, for being able to penetrate, even partially, inside the holes or between the fibers, and this would cause a too low and fully unacceptable overall adhesive strength.

In the specific case it has been observed that, for having an optimum adhesion in structures in which at least one of the two substrates is a fibrous or perforated one, at the same time avoiding the Bleed Through, it is advisable that the hot-melt formulations of the present invention have a Rheological Setting Temperature Tx comprised between 30° C. and 80° C.

It is moreover advisable that, at that temperature, the value of the Crossover Modulus Gc is comprised between 0.01 MPa and 0.25 MPa, and preferably between 0.015 MPa and 0.20 MPa. Obviously, because the measurement of such parameters is performed in a rheological cycle that mimics the application of the molten adhesive, its spontaneous slow cooling and its solidification, with the formation of the adhesive bond, all these parameters are measured at Time Zero and at the frequency of 1 Hz, in a rheological experiment in decreasing temperature, between 170° C. and −20° C., at the cooling rate of 2° C./minute.

About the unexpected effectiveness of polyethylene waxes, especially the ones with low molecular weight and with a very narrow distribution of molecular weights (Mw/Mn very small), in controlling and stopping the Bleed Through in the present adhesive formulations based on a butene-1 polymer composition, in spite of the substantial chemical incompatibility and immiscibility of Polyethylene and Polybutene-1, it is reasonable to suppose that, without being linked to any theory, this just depends, from one side, on such basic incompatibility between Polyethylene and Polybutene-1; however, from the other side, it is also reasonable to suppose that this unexpected effectiveness depends also on a "partially/slightly reduced" incompatibility of these peculiar waxes, due to their very low molecular weight and to the very small Polydispersity Index.

I.e. it is reasonable to think that, if we should add to the present adhesive formulations based on Polybutene-1, a Polyethylene at high molecular weight or with a broad PDI, the incompatibility between the two polymers would be so strong that the Polyethylene would immediately demix and fully migrate on the surface of the adhesive, causing an immediate "freezing"/solidification (due to the high crystallinity of crystalline Polyethylenes). This fact would stop immediately the penetration, even a partial penetration, of the adhesive inside the holes or between the fibers of the substrate. In such conditions, surely there will be no Bleed Through; but however, because no penetration, not even a partial one, has occurred, and there is not any "mechanical interlocking" between adhesive and substrate, the observed adhesive strength would be unacceptably low, because of the reduced contact area between the adhesive and the substrate.

If, on the contrary, we would add, as e.g. done in WO2018/007451A1 a polypropylene wax, that is fully compatible and miscible with the formulations based on Polybutene-1, no effect on Bleed Through would be observed: the polypropylene wax would solubilize inside the molten formulation and this would, in most cases, continue to flow, setting slowly and so potentially causing Bleed Through.

Whereas, a polyethylene wax (i.e. chemically incompatible), that however has a sufficiently low molecular weight and an Mw/Mn also very small (all factors that on the contrary favor a partial "decrease of the incompatibility"— see below) will behave in an intermediate and balanced way.

In fact, because the polyethylene wax is anyhow incompatible, a fraction of it will in any case demix and bleed on the surface of the adhesive, favoring anyhow a relatively quick setting and therefore avoiding the Bleed Through.

However, thanks to a partial "decrease of the incompatibility", due to the low molecular weight and to the very small Polydispersity Index, said demixing will occur more slowly than in the previous case of Polyethylenes at high molecular weight and high PDI. In this way the setting rate of the adhesive is tuned at a level such that, from one side, it is sufficiently quick to avoid the Bleed Through; on the other side it is also not excessively quick, and therefore it allows a partial penetration of the adhesive inside the holes and voids of the substrate, in this way allowing to achieve a high adhesive strength even for these substrates that are very difficult to be strongly bonded.

About the fact that, in incompatible polymer blends, higher molecular weights tend to increase the incompatibility; while lower molecular weights and smaller Polydispersity Indexes tend to reduce it (without of course fully eliminating it) one can see for example what is stated in the book "Polymer Blends" by D. Paul and S. Newman, especially in Volume I, chapter II, book that is herein incorporated as a reference.

The optimum performances in preventing the Bleed Through of the adhesive formulations according to the present invention and that comprise less than 5% by weight of one or more polyethylene waxes, especially the ones having the above mentioned peculiar properties, even when used on perforated, fibrous or porous substrates, are demonstrated in the "Bleed Through Test" that will be described in details below.

At this point, it is essential to emphasize that all the hot-melt formulations according to the present invention, owed to the combination between the above described butene-1 polymer compositions, and levels of viscosity modifiers that are exceptionally lower, compared to what normally taught and practiced for similar adhesives by the prior art and by the industrial practice, always have adhesive and cohesive properties that are optimal and surprisingly improved, as demonstrated by the fact that all of them pass the severe Hang Time test, as described later.

However, some of them, that do not comprise any polyethylene wax, as the ones described above and that have particular thermal and rheological properties, may have a non-optimized behavior regarding the Bleed Through phenomenon. Also these latest formulations are to be considered in any case as excellent adhesives, at very high and improved adhesiveness and cohesion; but they are preferably to be utilized in uses in which the phenomenon of the Bleed Through can't occur (e.g. in the bonding of two non-perforated substrates, like two plastic films) or in which the Bleed Through, even if present, is not a critical phenomenon e.g. inside laminates that, for their particular position inside an absorbent article, cannot adhere to other elements of the article, or in laminates that during use cannot contact the skin of the user etc.).

In all the other applications, in which at least one of the two substrates is fibrous or perforated, it is more advisable to use adhesive formulations according to the present invention, in the version also comprising at least one polyethylene wax.

Tackifiers

In an embodiment of the present invention, the adhesive compositions of the present invention also comprise at least one tackifying resin, having a Ring & Ball softening point comprised between 5° C. and 160° C.

Among all the possible families of tackifiers, well known in the field of hot-melt adhesives, the preferred ones in the formulations of the present invention, belong to those families that are more compatible with Polybutene-1 and basically with polyolefins.

In general the tackifiers comprised in the formulations of the present invention can be selected among the aliphatic hydrocarbon tackifiers, and their partially or fully hydrogenated derivatives; the aromatic hydrocarbon tackifiers, and their partially or fully hydrogenated derivatives; the aliphatic/aromatic tackifiers, and their partially or fully hydrogenated derivatives; the terpenic tackifiers, and their partially or fully hydrogenated derivatives; the rosins, their esters and their partially or fully hydrogenated derivatives. Fully hydrogenated hydrocarbon tackifiers, both aliphatic and aromatic and aliphatic/aromatic, are particularly preferred because they have an optimum compatibility with the isotactic metallocene polymer compositions, at low viscosity and with a bimodal compositions, that are used in the hot-melt adhesives according to the present invention.

Furthermore it has been discovered that it is preferable that the tackifying resins, used in the formulations of the present invention, have a Ring & Ball softening temperature comprised between 70° C. and 135° C., preferably between 80° C. and 130° and more preferably between 85° C. and 125° C.

Particularly preferred tackifiers in the present invention are highly purified tackifiers that contain extremely low quantities of impurities and monomeric volatile components like xylene, toluene, hexane, vynil-toluene, indene etc. that contribute to generate bad odors in the final finished product and to decrease the thermal stability of the tackifying resin. Said volatile compounds are measured by ionic Gas-Chromatography with head-space by heating a 2 grams samples of the resin for 30 minutes at 190° C. with a head-space equal to 20 ml. In the present invention, tackifiers containing a level of volatiles not greater than 5 ppm (parts per million), preferably not greater than 2 ppm and more preferably non greater than 1 ppm are particularly preferred. Industrial examples of said tackifiers having a very low content of volatile impurities are e.g. the tackifiers supplied by Eastman (USA) under the trade mark Ultra Pure.

In the embodiment of the present invention in which the hot-melt adhesive formulations comprise at least one tackifying resin, they comprise between zero and 75% by weight of at least one tackifier or of a blend of tackifiers, preferably between 10% by weight and 70% by weight, and more preferably between 20% by weight and 65% by weight.

Other Additional Components

The hot-melt adhesive formulations according to the present invention preferably do not comprise other polymers different from the novel metallocene butene-1 polymer composition at low viscosity and with a substantially bimodal composition, apart from what disclosed below for specific particular polymers.

In particular, the present adhesives preferably do not contain amorphous alpha-polyolefins (APAO), often utilized by prior art in adhesives, where they are blended with non-metallocenic old-generation Polybutenes-1. Said APAO's are e.g. marketed by Rextac under the same trade mark Rextac; or by Evonik under the trade mark Vestoplast.

Furthermore, the present adhesives preferably do not contain semi-crystalline polymers, especially semi-crystalline heterophase copolymers of propylene and ethylene, marketed by ExxonMobil under the trade mark Vistamaxx or by LyondellBasell under the trade mark Hifax.

However, if it is advisable, for whatever reason, to add small quantities of the above mentioned polymers or of other polymers different from the isotactic metallocene butene-1 polymer compositions, that are the polymeric base of the present adhesives, in any case the overall content of these polymers, different from the metallocene Polybutenes-1, is not greater than 15% by weight of the total hot-melt formulation, and preferably is not greater than 10%.

Moreover the hot-melt adhesive formulations according to the present invention, that comprise, as their main polymeric constituent, at least one isotactic metallocene butene-1 polymer composition, that has a low viscosity and that has a substantially bimodal composition, directly obtained during polymerization, in two consecutive and separate reaction steps, according to what previously described, may also comprise, as secondary optional polymeric constituent and in a quantity not greater than 15% by weight, isotactic metallocene homopolymers or copolymer of butene-1 having a monomodal composition and a low viscosity. The low viscosity of said isotactic metallocene monomodal homopolymers or copolymers of butene-1, is expressed by their Melt Flow Rate, measured according to ISO 1133 at 190° C., that is comprised between 200 and 4,000 g/10 minutes and preferably between 400 and 3,000 g/10 minutes.

The hot-melt adhesive formulations according to the present invention may further comprise between 0.01% by weight and 10% by weight of at least one stabilizer like anti-oxidants, UV photo-stabilizers and their blends. Furthermore, they can comprise up to 15% by weight of other optional additional components, like mineral fillers, pigments, dyes, perfumes, surfactants, antistatic agents.

Further Properties of the Adhesive Formulations According to the Invention

As already mentioned, the adhesive, mechanical and rheological properties of the hot-melt adhesive formulations according to the present invention change and significantly improve with time, due to the slow spontaneous crystallization of the peculiar metallocene butene-1 polymer compositions, having a bimodal composition, that are their main polymeric constituent, crystallization that occurs spontaneously at room conditions and that completes in from about one to seven days, typically in about five days.

Therefore all the tests and all the properties of the present adhesives, and of the bonded structures containing said adhesives, are generally performed and measured "at five days"; i.e. are intended to be performed and measured, at 23° C. and 50% relative humidity, on samples that have been kept for five days in a climatic room at 23° C. and 50% relative humidity, counting said five days from the setting from the molten state of the hot-melt adhesive, and therefore also from the production of the bonded structures containing such adhesive. These are in fact, in the real use, the conditions that will be seen by a future user, e.g. inside a hygienic absorbent article, that never arrives to a final user before a few months since its date of manufacturing.

What said above, obviously doesn't apply to properties and test that are said to be specifically performed "at Time Zero" or "in initial conditions", with the aim e.g. of examining behaviors that regard the formation of the adhesive bond, that occurs at Time Zero, or to compare and quantify the changes in properties and behaviors that just occurs between Time Zero and five days.

In particular about the rheological parameters and the Enthalpies of Crystallization or of Crystalline Melting of the present adhesive formulations, it can be stated that:

The rheological parameters at Time Zero, are measured, at the frequency of 1 Hz, in a rheological experiment, in decrease of temperature, between 170° C. and −20° C., at the cooling rate of 2° C./minute. These conditions mimic very well the behaviors of the adhesive when, at time zero, it is applied from the melt on a substrate and it spontaneously and slowly cools and solidifies, forming the adhesive bond;

The rheological parameters "at five days" are measured, at the frequency of 1 Hz, in a rheological experiment, with increase of temperature, between −20° C. and 170° C., at the heating rate of 2° C./minute, on samples aged for five days at 23° C. and 50% relative humidity;

The Crystallization Enthalpies from the melt, at Time Zero, are measured by a DSC test, according to ASTM D 3417-99, in a test with decrease of temperature between 180° C. and −70° C., at the cooling rate of 1° C./minute;

The Enthalpies of Crystalline Melting, at five days, are measured by a DSC test, according to the same ASTM method, in a test with increase of temperature between −70° C. and 180° C., at the heating rate of 1° C./minute, on samples aged for five days at room conditions.

Moreover, the hot-melt adhesive formulations according to the present invention are characterized by at least one of the following parameters and behaviors:

A Crystallization Enthalpy from the melt at time zero, measured by a DSC test according to ASTM D 3417-99 at the cooling rate of 1° C./minute, that is not greater than 20 J/g, preferably not greater than 15 J/g, and more preferably not greater than 10 J/g. This sufficiently low Crystallization Enthalpy at Time Zero, is related to the fact that, during the solidification from the melt and the formation of the adhesive bond, the Polybutene-1 crystals of "Form II" that can be created in this phase, are in any case few. Hence the adhesive is initially prevailingly amorphous and so it is sufficiently soft and tacky for wetting well the substrates and so for forming strong adhesive bonds.

A Crystalline Melting Enthalpy at five days, measured by a DSC test according to ASTM D 3417-99 at the heating rate of 1° C./minute, ranging between 1 J/g and 35 J/g, and preferably between 3 J/g and 30 J/g. In a particularly preferred embodiment of the present invention, said Crystalline Melting Enthalpy results from the sum of at least three endothermic melting peaks, that can be both completely separate and distinct or partially superimposed. This much higher Crystalline Melting Enthalpy at five days assures that, during the aging at room temperature, the possible few initial crystals of the Form II of Polybutene-1 transform into stable Form I crystals, that are more resistant both thermally and mechanically, while also many new crystals of Form I are created, so to strongly increase both the final cohesion and adhesion of the adhesive. Without being linked to any theory, in the preferred embodiment of the present invention, in which more than one peaks of crystalline melting are present, the presence of multiple melting peaks is probably due to the fact that, together with the pure crystals of the Form I of Polybutene-1, the adhesive formulation may contain also smaller fractions of different crystals, deriving both from the presence of a copolymer inside the butene-1 polymer compositions, and from the interaction of Polybutene-1 with other constituents of the present adhesive formulations. While the crystals of Form I of Polybutene-1, that have the highest melting point and that are the most mechanically robust, contribute especially to the very high cohesion of the adhesive, the other lower melting crystals of mixed phases, just for their lower melting temperature, help an optimum adhesiveness, favoring the wetting of the substrate and so s strong adhesive bond.

An "Open Time", i.e. the period of time, after its application from the melt on a first substrate, during which the adhesive is able to form sufficiently strong adhesive bonds for the intended use, with a second substrate that is brought into contact under moderate pressure with the first one, that is not shorter than 1 minute and is preferably not longer than 120 minutes. The Open Time at Time Zero is measured according to ASTM D 4497-94 in the conditions that have been already specified in details.

A Ring & Ball Softening temperature at five days that is not greater than 130° C., preferably not greater than 120° C. and more preferably not greater than 110° C. It is measured according to ASTM D 36-95.

A Needle Penetration at five days, measured at 55° C. according to ASTM D 1321-04, ranging from 10 dmm and 100 dmm.

The Hang Time Test or Hang-Test

As already mentioned, the hot-melt adhesive formulations according to the present invention show at the same time excellent adhesion and excellent cohesion, substantially and surprisingly improved compared to the prior art. Said combination of high adhesion and high cohesion allows their use in particularly critical uses, like the bonded laminate structures forming the outside impermeable layer of a baby-diaper, uses in which other adhesives, that seem apparently similar, actually fail.

As said, the particular criticality and difficulty of such uses derive from the fact that e.g. said laminate structures are exposed, during use, to stresses that are not only especially high as an absolute value, but that are also applied according to solicitation-angles that continuously change in time and that practically can vary between zero degrees and 180 degrees.

Hence it makes no sense and it does not even mimics correctly these particularly critical conditions of use, to test the adhesive separately for its adhesive properties and its cohesive properties, as it is done in the great majority of the prior art. In fact, generally in the great majority of the prior art this is made by measuring, just in a separate way, from one side the adhesive properties through the so-called "Peel Strength"; and from the other side, the cohesion of the adhesive through the so-called "Shear Strength", in two independent tests, that are both performed with angles of application of the stress that are fixed and constant in time.

More specifically, the Peel Strength, that is defined as the average strength per unit of width needed to separate, at a controlled and constant speed, two substrates, bonded by the adhesive under test, is generally measured according to ASTM D 1876-01, by imposing a fixed angle for the application of the debonding force, angle that is equal to 90 degrees or sometimes to 180 degrees; the Shear Strength is generally measured according to ASTM D 3654-02, a test method in which it is measured the time needed to debond, from a rigid and vertical substrate (e.g. a vertical steel plate) another substrate, bonded to the first one by the adhesive under test, which is stressed vertically (so, according to a fixed and constant angle equal to zero degrees) by a stress directed according to gravity, for example a weight hung to the second substrate.

Both these tests give therefore two separate measures of the adhesiveness and of the cohesion of the tested adhesive, measured according to angles, for the application of the debonding stress, that are constant in time, and are equal generally to 90 degrees for the adhesiveness and to zero degrees for the cohesion.

On the contrary, as it is well known to any person averagely skilled in the technology of adhesives, in particularly severe applications, in which the solicitation angle of the stress is continuously variable, the behavior of the adhesive, in its elements of adhesion and cohesion, is really far away from being expressed by a simple sum of its "Peel Strength" and its "Shear Strength", both measured independently, according to angles that are fixed and constant in time, and that are different in the two tests.

Already other inventors, who dealt with hygienic absorbent articles and with the bonded structures used in them, have emphasized the inadequacy of the separate tests of Peel Strength and of Shear Strength, for measuring, in conditions closer to the real use, the overall resistance of said bonded structures, especially in the most critical uses, like the outside impermeable layer of a baby-diaper.

For checking their resistance even in such particularly critical uses, it has been proposed a much more severe test that subjects the real bonded structure, as used into the absorbent article, at the same time to "peel stresses" and to "shear stresses" according to angles that are variable in time, like it also happens in the real use.

In the industrial practice and patent literature, this much more severe test is called with different names, like "Hang Test", "Hang Time Test", "Peel Hang Time Test", "Shear Hang Time Test" and so on, even if, as said, it is neither to be compared nor to be confused with a classical "pure Peel" test, according to ASTM D 1876-01, or with a classical "pure Shear" test, according to ASTM D 3654-02.

An example of application of this severe "Hang Test" or "Hang Test Time", used for testing the resistance of laminate bonded structures to be utilized in an absorbing diaper, can be found e.g. in the patent U.S. Pat. No. 9,084,699.

In general, this test measures the time needed to debond and to open a certain area of a bonded structure, when a fixed weight is suspended to one of the two substrates, and all the structure is allowed to freely hang under the stress of the weight. In particular the Hang Time Tests differs from the Shear Test according to ASTM D 3654-02, because in the Shear Test the weight stresses the bonded structure in a direction that is rigorously vertical, and so according to an angle constant in time and equal to zero degrees, while in the Hang Time Test both the two substrates of the sample are freely hanging.

Hence, the angle according to which the weight, suspended to one of the two substrates, stresses the adhesive is not fixed a priori; it rather depends from the angle that the two specific substrates assume, while freely hanging under the action of the weight, depending therefore on their single stiffness; moreover said angle may change in time, while the two substrates gradually debond and open under the action of the load, which therefore makes a contemporary action of Peel and of Shear.

More specifically, in the present invention the Hang Time Test is performed in the following way: on a pilot line a laminate bonded structure is made, formed by a polyethylene film, having a basis weight of 23 $g/m^2$, available from Poligof (Italy), and a spunbonded polypropylene nonwoven, having a basis weight of 12 $g/m^2$, available from Union Industries (Italy).

The bonding is made by slot-die coating the adhesive under test at the temperature of 160° C. and at the basis weight of 1.0 $g/m^2$, on a pilot line that mimics the operating conditions of an industrial line and that is operated at the speed of 250 m/minute.

The molten adhesive is coated on the nonwoven, because the polyethylene film could deform or could be holed by a direct contact with the molten adhesive; after the coating the nonwoven is immediately put in contact with the plastic film to which it adheres.

The laminate is then aged for five days under room conditions. After this time, one cuts from every laminate, five rectangular strips having a width of 100 mm and a length of 80 mm.

Each strip is tested at 23° C. in the following way: the strip is opened at one of its widest ends, debonding the two substrates one from the other and opening them for a length of 30 mm; if necessary, said opening of the strip can be facilitated by dissolving with petroleum ether the adhesive present in the area that must be opened.

One marks, with a transversal line made with black indelible ink, both the starting point of the part of laminate that is still perfectly bonded, as well as also a distance from this line, inside the still bonded part, equal to 40 mm.

After this, the open end of the polyethylene film is suspended with a clamp to a fixed metallic support, positioned at a height from the floor or from a lower plane of at least 500 mm. On the contrary, the other open end of the nonwoven is splayed in the opposite direction of the plastic film, and is allowed to hang perfectly free. At this end it is then suspended by a clamp a weight, so that the overall load (weight plus clamp) hung to the free end of the nonwoven is globally 150 g.

The sample is allowed to freely hang and the chronometer is started. Under the action of the weight, the opening of the sample of laminate begins and goes on, under the contemporary action of Peel and Sheer stresses. The chronometer is stopped when said opening of the sample reaches the second transversal line, positioned at 40 mm from the initial line, and the time in minutes is recorded. The test is repeated on five samples of each laminate. The Hang Time of the adhesive under test is calculated as the average value of the five times recorded for the five samples.

The results of the Hang-Time test for the adhesive formulations of the Examples, both according to the invention and comparative ones, are listed in Table 1 (see below).

Test to Qualitatively Measure Bleed Through

As said, in some applications that involve at least one fibrous or holed substrate (and even more when both substrates have holes, cavities or are fibrous), it is absolutely necessary to avoid the phenomenon called "Bleed Through" i.e. an excessive penetration of the semi-molten adhesive into the substrate, during the application, with even a possible surfacing of a part of the adhesive on the opposite side of the perforated or fibrous substrate.

The behavior of the tested adhesive towards Bleed Through is checked herein in very severe conditions, i.e. using a fibrous substrate that is particularly thin and open. Specifically the phenomenon is herein checked on a bonded structure formed by a polypropylene nonwoven, having a basis weight of 12 $g/m^2$, available from Union Industries (Italy), to which a polyethylene film, having the basis weight of 16 $g/m^2$, available from Poligof (Italy), is bonded.

On a pilot line, mimicking the operating conditions of an industrial line and at the speed of 250 m/minute, the adhesive is sprayed at the temperature of 160° C. and at the basis weight of 6.0 $g/m^2$. The adhesive is sprayed on the nonwoven that is more resistant to high temperatures, and then it is immediately contacted with the plastic film on which it adheres.

The test is stopped when the roll of formed laminate has an overall outer diameter of about 200 mm. The roll is aged for five days at 23° C. and 50% Relative Humidity. After such aging, the roll is manually unwound and a qualitative ranking for the possible "Bleed Through" is given, on the basis of a four level ranking (High; Medium; Low; Null), depending on the observed resistance to unwinding and blocking, as well as on the possible noise from debonding the stuck layers inside the roll. In fact, if the tested adhesive bleeds through the fibrous substrate, it will stick together adjacent layers of the laminate inside the roll; and this lower or higher sticking, proportional to the amount of bleed-through of the adhesive, is also proportional to the observed resistance to unwinding and to the noise.

EXAMPLES

The present invention is better illustrated by the following examples, which are given herein merely for the purpose of illustration and are not to be regarded as limiting the scope of the invention or the manner in which it can be practiced. Unless specifically indicated otherwise, parts and percentages are given by weight.

However, before illustrating a few examples, both according to the invention and comparative ones, it is opportune to recall again that the present invention has surprisingly discovered that:

unusually low levels of viscosity modifiers cause contemporary optimal values of high adhesiveness and cohesion, a situation well expressed by excellent values of Hang Time;

nevertheless, only the presence also of peculiar polyethylene waxes, that are partially incompatible with the base polymer and that are disclosed herein, can allow to get rid even of the highly negative phenomenon known as Bleed Through.

Hence, in order to avoid misunderstandings, it is necessary to emphasize that only formulations that combine both the two above mentioned formulation criteria are Examples "fully according to the present invention" because they have at the same time an optimum Hang-Time and an optimum resistance to Bleed Through.

Therefore the below disclosed examples that, even in the presence of low levels of viscosity modifiers, do not comprise the aforementioned peculiar polyethylene waxes, or comprise waxes having a different chemical nature and structure, are to be considered as "according to the invention" exclusively for the excellent Hang Time and so for the combination between high adhesiveness and cohesion.

These latest formulations can be satisfactorily used just when it is not present at least one fibrous or perforated substrate, because on such holed substrates said formulations might anyhow give a non-null level of Bleed Through.

EXAMPLES ACCORDING TO THE INVENTION

Example 1

The following hot-melt adhesive formulation has been prepared by mixing the ingredients in the molten state at 170° C.:

| Ingredient | % by weight on the total weight of the adhesive formulation | Nature and Supplier |
| --- | --- | --- |
| Koattro PB M 1500M | 49.5 | Bimodal isotactic metallocene butene-1 polymer composition available from LyondellBasell |
| Regalite R 1100 | 44.7 | Fully hydrogenated hydrocarbon tackifier available from Eastman |
| Primol 352 | 3.8 | Viscosity Modifier (paraffinic mineral oil) available from ExxonMobil |
| Irganox 1010 | 2.0 | Antioxidant available from BASF |

The hot-melt adhesive formulation of Example 1 comprises an exceptionally small quantity, and precisely just 3.8 by weight, of a viscosity modifier that is not solid at room temperature. The formulation disclosed in the present example has an excellent toughness, expressed also as an unusual ability in dissipating the imposed energy in the Stress-Strain to Break test.

In fact, its toughness, at 23° C. and 0.01 Hz and after five days of aging, equals 0.84 $MJ/m^3$; the elongation at break is 348%; the maximum stress in said curve (peak) is 0.41 MPa. Moreover, the Elastic Modulus G' at 23° C. and 1 Hz, after five days of aging, is equal to 7.7 MPa.

Therefore, the hot-melt adhesive formulation of Example 1 shows at the same time an optimum adhesiveness and cohesion, as also demonstrated by the excellent result of the Hang Time test, that is equal to as much as 105 minutes (Table 1).

However, the present formulation, because it doesn't comprise any peculiar polyethylene wax, does not possess fully optimized rheological characteristics so to completely avoid a possible Bleed Through even in the presence of highly holed substrates. In fact, this formulation is at the limit of acceptability in the above described Bleed Through test, in which it shows a non-null level of Bleed Through, between low and medium (Table 2). It has also a rather long open time equal to 100 minutes.

This ability of the present formulation of partially flowing through perforated and fibrous substrates, and of remaining tacky for a relatively long time, is highlighted also by its main rheological parameters at Time Zero. Indeed, it shows a Rheological Setting Temperature Tx (crossover temperature) equal to 35° C. and a Crossover Modulus at said temperature, Gc, equal to 0.015 MPa.

In addition, even if the level of viscosity modifier is uncommonly small, the formulation in this example shows a viscosity at 170° C. as low as 2,000 mPa·s, that is comparable to the viscosity of similar formulations containing a much higher level of alike additives at low molecular weight.

About other main properties of the formulation of Example 1, it has a crystallization enthalpy from the melt at time zero that is not detectable by DSC; a crystalline melting enthalpy after five days of aging that is equal to 7.4 J/g and that shows three melting peaks with a maximum central temperature of 76.5° C.; a Ring & Ball temperature of 85.7° C.; a Needle Penetration at 55° C. and after five days of aging equal to 70 dmm.

Example 2

The following hot-melt adhesive formulation has been prepared by mixing the ingredients in the molten state at 170° C.:

| Ingredient | % by weight on the total weight of the adhesive formulation | Nature and Supplier |
| --- | --- | --- |
| Koattro PB M 1500M | 49.0 | Bimodal isotactic metallocene butene-1 polymer composition available from LyondellBasell |
| Regalite R1100 | 44.2 | Fully hydrogenated hydrocarbon tackifier available from Eastman |
| Primol 352 | 3.8 | Viscosity Modifier (paraffinic mineral oil) available from ExxonMobil |
| Polywax 850 | 1.0 | Polyethylene homopolymeric wax available from Baker Hughes |
| Irganox 1010 | 2.0 | Antioxidant available from BASF |

The hot-melt formulation of Example 2 is similar to the formulation of the previous Example, with still the same very low level of viscosity modifier, and with the addition of merely 1.0% by weight of a peculiar polyethylene wax, that has a fully linear structure, an average Number Molecular Weight equal to 850, and a Polydispersity Index Mw/Mn that is exceptionally small and as low as 1.08. Said quantity, however small, of said peculiar polyethylene wax, that is partially incompatible with the base metallocene butene-1 polymer composition, gives to the present formulation also an excellent behavior in the Bleed Through test, with a completely null level of observed Bleed Through (Table 2). Said optimal behavior for Bleed Through can be correlated also to a drastic decrease in the open time, caused by the introduction of such small quantity of this peculiar polyethylene wax, as well as to the rheological parameters at Time Zero. In fact, the open times decreases very much, compared to the previous Example, being as low as 3 minutes; while Tx is equal to 37.7° C. and its Crossover Modulus Gc is 0.051 MPa.

The above mentioned excellent behavior in Bleed Through is obviously associated with a still optimum combination of high adhesiveness and cohesion, as shown by a value, in the Hang Time test that is not only very high, but that is even significantly improved towards the already excellent value of the previous Example 1. In fact, the Hang Time of the formulation of Example 2 is as long as 145 minutes.

Also here, this very long value of Hang Time can be correlated to excellent values in the Stress-Strain to Break curve. In fact, the area under said curve (toughness) is as much as 1.62 MJ/m$^3$; the elongation to break is 511%; the maximum load in the curve is 0.56 MPa. The optimum cohesion can be correlated also with the value of the Elastic Modulus G' at 23° C. and 1 Hz, after five days of aging, that is equal to 15.1 MPa.

About other important parameters characterizing the present formulation of Example 2, the Viscosity at 170° C. is 1,915 mPa·s; the crystallization enthalpy from the molten state at Time Zero is equal to 0.93 J/g; the crystalline melting enthalpy after five days of aging is 10.1 J/g and it is composed by the sum of three melting peaks with a maximum central temperature of 85.5° C. The Ring & Ball temperature of the above formulation is equal to 87.3° C. and its Needle Penetration at 55° C. is 67 dmm.

COMPARATIVE EXAMPLES

Comparative Example 1

The following hot-melt adhesive formulation of Comparative Example 1 has been prepared by mixing its ingredients in the molten state at 170° C. This formulation is similar to the previous Example 1, but it comprises a much higher level of the viscosity modifier (as much as about 3.5 times greater), according to what taught by a significant part of Prior Art.

| Ingredient | % by weight on the total weight of the adhesive formulation | Nature and Supplier |
| --- | --- | --- |
| Koattro PB M 1500M | 42.0 | Bimodal isotactic metallocene butene-1 polymer composition available from LyondellBasell |
| Regalite R 1100 | 43.0 | Fully hydrogenated hydrocarbon tackifier available from Eastman |
| Primol 352 | 13.0 | Viscosity Modifier (paraffinic mineral oil) available from ExxonMobil |
| Irganox 1010 | 2.0 | Antioxidant available from BASF |

The Comparative Example 1, that comprises a high level of a viscosity modifier, shows fully unacceptable adhesive and cohesive properties, as demonstrated by its very small Hang Time, that is as short as just 11 minutes. This very unsatisfactory result is highlighted even in the results of the Stress-Stress to Break test. In fact, the area under said curve (toughness) is unusually small and merely equal to 0.09 MJ/m$^3$; also the elongation to break is low and equal to 151%; and the maximum stress in the curve is just 0.12 MPa.

The formulation of the present comparative example, because it also does not comprise any peculiar polyethylene wax, disclosed in the present invention, has moreover a similar very bad behavior in the Bleed Through test (Table 2). This unacceptable level of Bleed Through can be also correlated to a very long open time, as long as 240 minutes, as well as to the parameters of the rheological curve in cooling at Time Zero, that are particularly bad. In fact, said curve does not show any crossing temperature of the two moduli, even by cooling to as low as −20° C. Even after five days of aging, the Elastic Modulus at 23° C. and 1 Hz continues to be quite low with a value of 2.7 MPa.

For the other main parameters of the present formulation, its viscosity at 170° C. is equal to 964 mPa·s; the Ring & Ball temperature is very low and equal to 63° C.; the Needle Penetration at 55° C. is excessively high (the adhesive is too soft) and it's equal to 118 dmm.

Comparative Example 2

The hot-melt adhesive formulation of the Comparative Example 2 is similar to the one of the previous comparative example, keeping the same high level of the viscosity modifier, according to what taught by a significant part of the Prior art.

However, in order to try to somehow obviate the extremely bad levels of adhesiveness and cohesion (and hence of Hang Time) of the previous comparative example, the bimodal isotactic metallocene butene-1 polymer composition Koattro PB M 1500M, used above, is substituted by an analogous bimodal isotactic metallocene butene-1 polymer composition Koattro PB M 0600M, that has a substantially higher molecular weight and crystallinity. However, as showed below, even such substitution, still in the presence of the same excessive level of viscosity modifier, is unable to remove the same very negative behaviors, already shown by Comparative Example 1.

| Ingredient | % by weight on the total weight of the adhesive formulation | Nature and Supplier |
| --- | --- | --- |
| Koattro PB M 0600M | 42.0 | Bimodal isotactic metallocene butene-1 polymer composition available from LyondellBasell |
| Regalite R 1100 | 43.0 | Fully hydrogenated hydrocarbon tackifier available from Eastman |
| Primol 352 | 13.0 | Viscosity Modifier (paraffinic mineral oil) available from ExxonMobil |
| Irganox 1010 | 2.0 | Antioxidant available from BASF |

In fact, also in the present case, the combined properties of adhesiveness and cohesion continue to prove strongly unsatisfactory, as highlighted by the still bad value of Hang Time. Indeed, the formulation of the present comparative example has a Hang Time of just 28 minutes. In spite of an apparently sufficient toughness of 1.09 MJ/m$^3$ and of a maximum stress in the Stress-Strain curve of 0.97 MPa, the present adhesive formulation fails mainly because of its very low elongation to break, that is as small as just 136%. Its Elastic Modulus G' at 23° C. and 1 Hz is equal to 14.1 MPa.

Moreover, like the formulation of the previous comparative example, also the present adhesive formulation has very unsatisfactory rheological parameters at Time Zero, in spite of the significantly higher molecular weight and higher crystallinity of the base polymer, as highlighted by the melting enthalpy equal to 15.3 J/g. In spite of this, the above disclosed adhesive formulation has a very low Rheological Setting Temperature Tx that is just equal to 26° C., barely above room temperature, and a corresponding Gc value of 0.011 MPa.

The present adhesive has moreover a very bad behavior in the Bleed Through test, where the level of Bleed Through remains unacceptably high (Table 2) practically identical to the one of the previous comparative example.

The remaining main parameters characterizing the above adhesive formulation are: a viscosity at 170° C. equal to 2,050 mPa·s; an open time of 120 minutes; a Ring & Ball temperature of 78° C. and a Needle Penetration at 55° C. equal to 58 dmm.

Comparative Example 3

| Ingredient | % by weight on the total weight of the adhesive formulation | Nature and Supplier |
| --- | --- | --- |
| Koattro PB M 1500M | 49.0 | Bimodal isotactic metallocene butene-1 polymer composition available from LyondellBasell |
| Regalite R 1100 | 44.2 | Fully hydrogenated hydrocarbon tackifier available from Eastman |
| Primol 352 | 3.8 | Viscosity Modifier (paraffinic mineral oil) available from ExxonMobil |
| Epolene N-15 | 1.0 | Polypropylene homopolymeric wax available from Westlake Chemical Co. |
| Irganox 1010 | 2.0 | Antioxidant available from BASF |

Scope of the present Comparative Example 3 is to show that the use of waxes, that are different from the peculiar polyethylene waxes disclosed herein, that are partially incompatible with the base butene-1 polymer composition, has no effect in decreasing or stopping the Bleed Through phenomenon.

In particular, the formulation of the present Comparative Example 3 repeats the formulation of the previous Example 2, according to the invention, but it substitutes the peculiar and partially incompatible polyethylene wax with a polypropylene wax that, on the contrary, is very compatible with the base polybutene 1.

The above shown formulation of Comparative Example 3 is therefore to be considered as an "example according to the invention" just for what concerns the excellent value of Hang Time, due to its very low content of viscosity modifier; but the above formulation is at the same time also an unsatisfactory "comparative example" for what concerns the behavior in the Bleed Through test, that it not at all improved by the addition of the polypropylene wax, and on the contrary it is even a bit worsened, compared e.g. to the above Example 1, according to the invention, that does not comprises any wax.

What asserted above can also be summarized as follows: the formulation of Comparative Example 3 has a very good value of Hang Time equal to 86 minutes, that can be correlated to good parameters in the Stress-Strain to Break curve. In fact, the area under said curve (toughness) is equal to 0.74 MJ/m$^3$; the elongation to break is 265%; the maximum stress in the curve is 0.60 MPa. The good cohesion can be also expressed by the Elastic Modulus G', at 23° C. and 1 Hz, after five days of aging, that is equal to 18.1 MPa;

on the contrary, the same formulation has an unacceptable level of Bleed Through (Table 2). This can be also correlated to the fact that its rheological diagram in cooling and at Time Zero, does not show any crossing temperature of the two moduli, Tx, even by cooling the material as low as to −20° C. Also the open time of the present formulation is quite long and equal to 105 minutes.

For what concerns the other main parameters of the above formulation, its viscosity at 170° C. is 1,950 mPa·s; its Ring & Ball temperature is 86.9° C.; and its Needle Penetration at 55° C. is equal to 65 dmm.

TABLE 1

| Adhesive Formulation | Hang-Time at 1 g/m$^2$- 150 g load (minutes) |
| --- | --- |
| Example 1 | 105 |
| Example 2 | 145 |
| Comparative Example 1 | 11 |
| Comparative Example 2 | 28 |
| Comparative Example 3 (Comparative Example just for Bleed-Through) | 86 |

TABLE 2

| Adhesive Formulation | Bleed-Through level |
| --- | --- |
| Example 1 | Low/Medium |
| Example 2 | Null |
| Comparative Example 1 | High |
| Comparative Example 2 | High |
| Comparative Example 3 (Comparative Example just for Bleed-Through) | Medium |

What is claimed is:
1. A hot-melt adhesive formulation comprising:
a) an isotactic metallocene butene-1 polymer composition having a melt flow rate (MFR) ranging between 200 and 6,000 g/10 minutes, measured at 190° C. and under a weight of 2.16 kg, which has a bimodal-type composition comprising:
A) an isotactic butene-1 homopolymer or a butene-1 isotactic copolymer with one or more comonomers, selected from ethylene and alpha-olefins with a number of carbon atoms equal to or greater than three, said homopolymer or copolymer A, having a comonomer copolymerised content (CA) not greater than 5% by mole; and
B) a butene-1 isotactic copolymer with one or more comonomers selected from ethylene and alpha-olefins with a number of carbon atoms equal to or greater than three, said copolymer B, having a comonomer copolymerized content (CB) between 6% and 25% by mole;

wherein the polymer composition has a total content of copolymerized comonomer, referring to the sum of A) plus B), between 3% and 18% by mole; and b) less than 5% by weight of a viscosity modifier which is not solid at room temperature or of a blend of viscosity modifiers which are not solid at room temperature.

2. The hot-melt adhesive formulation according to claim 1, which comprises not more than 4.5% by weight of a viscosity modifier which is not solid at room temperature or of a blend of viscosity modifiers which are not solid at room temperature.

3. The hot-melt adhesive formulation according to claim 1, wherein the homopolymer or copolymer A has a copolymerised comonomer content (CA) not greater than 4% by mole.

4. The hot-melt adhesive formulation according to claim 1, wherein the copolymer B has a copolymerized comonomer content (CB) between 8% and 20% by mole.

5. The hot-melt adhesive formulation according to claim 1, wherein the metallocene butene-1 polymer composition has a total content of copolymerised comonomer, referring to the sum of A) plus B), between 5% and 15% by mole.

6. The hot-melt adhesive formulation according to claim 1, wherein the metallocene butene-1 polymer composition has a content of fraction soluble in xylene at 0° C. of not less than 65% by weight, referring to the total weight of A) plus B).

7. The hot-melt adhesive formulation according to claim 6, wherein the metallocene butene-1 polymer composition comprises between 10% and 40% by weight of A) and between 60% and 90% by weight of B), referring to the total weight of A) plus B).

8. The hot-melt adhesive formulation according to claim 1, wherein the metallocene butene-1 polymer composition has a content of fraction soluble in xylene at 0° C. not greater than 60% by weight, referring to the total weight of A) plus B).

9. The hot-melt adhesive formulation according to claim 8, wherein the metallocene butene-1 polymer composition comprises between 35% and 65% by weight of A) and between 35% and 65% by weight of B), referring to the total weight of A) plus B).

10. The hot-melt adhesive formulation according to claim 1, wherein the metallocene butene-1 polymer composition has a Delta H TmII not greater than 20 J/g, measured with a temperature scanning ramp of 10° C./minute.

11. The hot-melt adhesive formulation according to claim 1, wherein the metallocene butene-1 polymer composition has a TmI of not less than 60° C.

12. The hot-melt adhesive formulation according to claim 1, wherein the metallocene butene-1 polymer composition has a viscosity ranging between 1,000 and 50,000 mPa·s, measured at 190° C.

13. The hot-melt adhesive formulation according to claim 1, wherein the metallocene butene-1 polymer composition has a polydispersity index not greater than 4.

14. The hot-melt adhesive formulation according to claim 1, wherein the metallocene butene-1 polymer composition has a Mw value of not less than 5,000.

15. The hot-melt adhesive formulation according to claim 1, wherein the metallocene butene-1 polymer composition has a glass transition temperature not greater than −10° C.

16. The hot-melt adhesive formulation according to claim 1, which has a Brookfield viscosity measured at a temperature of 170° C. which is not greater than 30,000 mPa·s.

17. The hot-melt adhesive formulation according to claim 1, which, after solidification by cooling from 170° C. to 23° C., has an open time not shorter than 1 minute.

18. The hot-melt adhesive formulation according to claim 1, which has, at Time Zero, a Crystallization Enthalpy from the melt, measured according to ASTM D 3417-99 and at the cooling rate of 1° C./minute, which is not higher than 20 J/g.

19. The hot-melt adhesive formulation according to claim 1, which has, after aging for five days, a Crystalline Melting Enthalpy, measured according to ASTM D 3417-99 and at the heating rate of 1° C./minute, ranging between 1 J/g and 35 J/g.

20. The hot-melt adhesive formulation according to claim 19, wherein the Crystalline Melting Enthalpy results from the sum of at least two endothermic melting peaks, which can be totally separate and distinct or partially superimposed.

21. The hot-melt adhesive formulation according to claim 1, which has a Ring & Ball softening temperature at five days not higher than 130° C.

22. The hot-melt adhesive formulation according to claim 1, wherein the isotactic metallocene butene-1 polymer composition constitutes from 10% by weight to 99.5% by weight of said hot-melt adhesive formulation.

23. The hot-melt adhesive formulation according to claim 1, wherein the viscosity modifier, which is not solid at room temperature, is selected from the group consisting of paraffinic mineral oils, naphthenic mineral oils, paraffinic and naphthenic hydrocarbons which are non-solid at room temperature, and mixtures of paraffinic and naphthenic hydrocarbons, oligomers which are not solid at room temperature of polyolefins and copolymers of the polyolefins, plasticizers which are not solid at room temperature, formed by esters, vegetable oils, natural fat, synthetic fat, and mixtures of natural fat and synthetic fats.

24. The hot-melt adhesive formulation according to claim 1, which also comprises at least one tackifier resin.

25. The hot-melt adhesive formulation according to claim 24, wherein the tackifier resin is selected from the group consisting of aliphatic hydrocarbon resins, aliphatic hydrocarbon resin derivatives that are partially hydrogenated, aliphatic hydrocarbon resin derivatives that are totally hydrogenated, aromatic hydrocarbon resins, aromatic hydrocarbon resin derivatives that are partially hydrogenated, aromatic hydrocarbon resin derivatives that are totally hydrogenated, aliphatic/aromatic hydrocarbon resins and derivatives thereof hydrogenated; polyterpenes and modified terpene resins, polyterpenes and modified terpene resin derivatives that are partially hydrogenated, polyterpenes and modified terpene resin derivatives that are totally hydrogenated, rosins, esters, ester derivatives that are partially hydrogenated, and ester derivatives that are fully hydrogenated.

26. The hot-melt adhesive formulation according to claim 24, wherein the at least one tackifier resin has a content of volatile compounds, extractable by heating at 190° C. for 30 minutes, that is not greater than 5 ppm.

27. The hot-melt adhesive formulation according to claim 24, wherein the at least one tackifier resin has a Ring & Ball softening temperature of not less than 70° C.

28. The hot-melt adhesive formulation according to claim 24, wherein the at least one tackifier resin comprises from zero to 75% by weight of said formulation.

29. The hot-melt adhesive formulation according to claim 24, which also includes less than 5% by weight of a wax.

30. The hot-melt adhesive formulation according to claim 29, wherein the wax is a polyethylene wax.

31. The hot-melt adhesive formulation according to claim 30, wherein the polyethylene wax comprises not more than 3% by weight of said formulation.

32. The hot-melt adhesive formulation according to claim 30, wherein the polyethylene wax has an average Number Molecular Weight not greater than 3,000.

33. The hot-melt adhesive formulation according to claim 32, wherein the polyethylene wax has a Polydispersity Index not greater than 2.5.

34. The hot-melt adhesive formulation according to claim 29, which comprises not more than 3% by weight of a polypropylene wax modified with maleic anhydride, said wax being added at a level such that, when a polyethylene wax is present, the overall content of the wax is not greater than 5% by weight.

35. The hot-melt adhesive formulation according to claim 1, which comprises not more than 15% by weight of a polymer or of a blend of polymers which are different than the metallocene butene-1 polymer composition.

36. The hot-melt adhesive formulation according to claim 35, wherein said polymer or blend of polymers is an amorphous alpha-polyolefin, or a heterophase semicrystalline copolymer of propylene and ethylene, or a blend of the amorphous alpha-polyolefin, the heterophase semicrystalline copolymer of propylene and ethylene.

37. The hot-melt adhesive formulation according to claim 36, wherein said amorphous alpha-polyolefin is a copolymer, a terpolymer or a tetrapolymer that has propylene or butene-1 as its main comonomer by weight; and wherein as a secondary monomer, one or more olefin(s) is selected among ethylene and other olefins between C3 and C8.

38. The hot-melt adhesive formulation according to claim 1, which also includes not more than 15% by weight of a homopolymer or copolymer of isotactic polybutene-1, having a monomodal composition and an MFR at 190° C. between 200 and 2,000 g/10 minutes.

39. The hot-melt adhesive formulation according to claim 38, wherein the homopolymer or copolymer of polybutene-1, having a monomodal composition, is synthesized by a metallocene catalyst.

40. The hot-melt adhesive formulation according to claim 1, which, after aging for five days at room conditions, has a Stress-Strain to Break curve, measured at 23° C. and 0.01 Hz, that has a toughness not lower than 0.2 $MJ/m^3$.

41. The hot-melt adhesive formulation according to claim 40, which has a maximum stress (peak) of a Stress-Strain to Break curve at 23° C. and 0.01 Hz, ranging from 0.15 MPa and 1.5 MPa.

42. The hot-melt adhesive formulation according to claim 40, which has an elongation to break at 23° C. and 0.01 Hz, not lower than 200%.

43. The hot-melt adhesive formulation according to claim 1, which, after aging for five days at room conditions, has an Elastic Modulus G', measured at 23° C. and 1 Hz, ranging from 3 MPa and 25 MPa.

44. The hot-melt adhesive formulation according to claim 1, which has a Rheological Setting Temperature Tx, measured at Time Zero and under cooling at a cooling rate of 2° C./minute, ranging from 30° C. and 80° C.

45. The hot-melt adhesive formulation according to claim 44, which has a Crossover Modulus Gc, measured at Time Zero and under cooling at the cooling rate of 2° C./minute, ranging from 0.01 MPa and 0.25 MPa.

46. The hot-melt adhesive formulation according to claim 1, which, after aging for five days at room conditions, has a Needle Penetration at 55° C. ranging from 10 dmm and 100 dmm.

47. The hot-melt adhesive formulation according to claim 1, which, in a Hang Time Test, performed on a bonded structure, aged for five days at room conditions, has a Hang Time value not lower than 60 minutes at the basis-weight of 1 $g/m^2$ and under a load of 150 g.

48. The hot-melt adhesive formulation according to claim 1, which is processable and applicable on a substrate, both by spraying and slot-die coating technologies, at a processing temperature not higher than 145° C., and which has a Brookfield viscosity, measured at 130° C., which is not higher than 15,000 mPa·s.

49. An absorbent hygienic article, comprising the hot-melt adhesive formulation according to claim 1.

50. The article according to claim 49, wherein said article is a baby-diaper, a training pants diaper, a diaper for incontinent adults, or a feminine catamenial pad.

51. The absorbent hygienic article according to claim 49, wherein the hot-melt adhesive formulation is used for at least one of the following uses: i) general construction adhesive of the whole article; ii) for bonding elastic components (threads, ribbons, films or elastic panels, etc.); iii) for strengthening and ensuring, even in use, the integrity of the absorbent core of the absorbent hygienic article; iv) for the bonding of perforated films both with a bidimensional or tridimensional structure; v) for the bonding of a nonwoven with another nonwoven or with a plastic film.

52. An article comprising the hot-melt adhesive formulation according to claim 1, wherein said article is selected from the group consisting of an absorbent surgical mattress, a sheet, a surgery laminate for medical use, and a wound-dressing product.

53. An article comprising the hot-melt adhesive formulation according to claim 1, wherein said article is selected from the group consisting of a mattress, and a component of the mattress.

54. An article comprising the hot-melt adhesive formulation according to claim 1, wherein said article is a packaging.

* * * * *